United States Patent
Leonard et al.

(10) Patent No.: US 6,529,776 B1
(45) Date of Patent: Mar. 4, 2003

(54) METHOD AND APPARATUS FOR REPOSITIONING A PERCUTANEOUS PROBE

(75) Inventors: Paul C. Leonard; Jon M. Bishay, both of Woodinville, WA (US)

(73) Assignee: Vertis Neuroscience, Inc., Seattle, WA (US)

( * ) Notice: Subject to any disclaimer, the term of this patent is extended or adjusted under 35 U.S.C. 154(b) by 0 days.

(21) Appl. No.: 09/666,931

(22) Filed: Sep. 21, 2000

Related U.S. Application Data

(63) Continuation-in-part of application No. 09/452,477, filed on Dec. 1, 1999, and a continuation-in-part of application No. 09/452,663, filed on Dec. 1, 1999, and a continuation-in-part of application No. 09/452,508, filed on Dec. 1, 1999, and a continuation-in-part of application No. 09/451,795, filed on Dec. 1, 1999, and a continuation-in-part of application No. 09/451,799, filed on Dec. 1, 1999, and a continuation-in-part of application No. 09/452,510, filed on Dec. 1, 1999, and a continuation-in-part of application No. 09/451,800, filed on Dec. 1, 1999, and a continuation-in-part of application No. 09/451,796, filed on Dec. 1, 1999, and a continuation-in-part of application No. 09/451,547, filed on Dec. 1, 1999.

(51) Int. Cl.$^7$ .................................................. A61N 1/05
(52) U.S. Cl. ...................................................... 607/116
(58) Field of Search .................................. 607/115, 116, 607/117; 600/373, 372, 382

(56) References Cited

U.S. PATENT DOCUMENTS

| | | | |
|---|---|---|---|
| 4,153,059 A | 5/1979 | Fravel et al. | |
| 4,284,856 A | 8/1981 | Hochmair et al. | |
| 4,381,012 A | 4/1983 | Russek | |
| 4,541,432 A | 9/1985 | Molina-Negro et al. | |
| 4,979,508 A | 12/1990 | Beck | |
| 5,417,719 A | * 5/1995 | Hull et al. | |
| 5,851,223 A | 12/1998 | Liss et al. | |
| 5,968,011 A | 10/1999 | Larsen et al. | |
| 6,117,077 A | 9/2000 | Del Mar et al. | |
| 6,269,270 B1 | 7/2001 | Boveja | |
| 6,304,785 B1 | * 10/2001 | McCreery et al. | |
| 6,355,021 B1 | 3/2002 | Nielsen et al. | |

* cited by examiner

Primary Examiner—Scott M. Getzow
(74) Attorney, Agent, or Firm—Perkins Coie LLP

(57) ABSTRACT

An apparatus for piercing a skin surface, and methods for operating and manufacturing such an apparatus. In one embodiment, the apparatus can include a support housing having an engaging surface to engage the skin surface. The support housing can include a first guide extending axially away from the engaging surface and a second guide extending transverse to the first guide. The apparatus can further include a probe coupled to a guide member with the guide member sequentially engaged with the first guide and the second guide to move in a first direction toward and away from the engaging surface without simultaneously moving in a second direction transverse to the first direction. Accordingly, a practitioner can reposition the probe from one location to the other (for example, by orbiting the probe relative to a central axis of the support body, or by translating the probe linearly relative to the support body) without moving the housing relative to the skin surface.

40 Claims, 11 Drawing Sheets

METHOD AND APPARATUS FOR REPOSITIONING A PERCUTANEOUS PROBE

CROSS REFERENCE TO RELATED APPLICATIONS

This application is a continuation-in-part of pending U.S. patent application Ser. Nos. 09/452,477, 09/452,663, 09/452,508, 09/451,795, 09/451,799, 09/452,510, 09/451,800, 09/451,796, and 09/451,547, all filed on Dec. 1, 1999.

TECHNICAL FIELD

The present invention relates generally to methods and apparatuses for repositioning percutaneous probes, such as percutaneous electrodes used for electrical nerve stimulation.

BACKGROUND OF THE INVENTION

Electrical therapy has long been used in medicine to treat pain and other conditions. For example, transcutaneous electrical nerve stimulation (TENS) systems deliver electrical energy through electrode patches placed on the surface of a patient's skin to treat pain in tissue beneath and around the location of the patches. One problem with TENS systems is that they may not provide patients with adequate pain relief.

More recently, a technique in which electrodes are placed through the patient's skin into the target tissue has been proposed. Percutaneous Neuromodulation Therapy ("PNT") (also sometimes called Percutaneous Electrical Nerve Stimulation or "PENS") using percutaneously placed electrodes achieves significantly better pain relief results than TENS treatments using skin surface electrodes. This therapy is described in Ghoname et al., "Percutaneous Electrical Nerve Stimulation for Low Back Pain," *JAMA* 281:818–23 (1999); Ghoname et al., "The Effect of Stimulus Frequency on the Analgesic Response to Percutaneous Electrical Nerve Stimulation in Patients with Chronic Low Back Pain," *Anesth Analg.* 88:841–6 (1999); Ahmed et al,. "Percutaneous Electrical Nerve Stimulation (PENS): A Complementary Therapy for the Management of Pain Secondary to Bony Metastasis," *Clinical Journal of Pain* 14:320–3 (1998); and Ahmed et al., "Percutaneous Electrical Nerve Stimulation: An Alternative to Antiviral Drugs for Herpes Zoster," *Anesth. Analg.* 87:911–4 (1998). The contents of these references are incorporated herein by reference.

One method for applying percutaneous nerve stimulation is to insert acupuncture needles into the patient's skin and attach the needles to waveform generators via cables and alligator clips to deliver a percutaneous electrical current. One drawback with this method is that the electrical connections to the needle may not be sufficiently secure and reliable. Another drawback with this method is that it may be difficult to accurately position the needles. For example, if a needle is placed too close to a nerve within a nerve region it is intended to treat, the needle itself may be painful and/or the amount of electrical current necessary to provide effective therapy may be painful. Accordingly, the practitioner may need to reposition the needle to a new location. However, it may be difficult for the practitioner to accurately reposition the needle. For example, the practitioner may lose track of the needle's original position once the needle is removed. Without having the original position of the needle as a reference, the practitioner may be unable to accurately locate the new position. Furthermore, the practitioner may not be able to accurately control the angle at which the needle re-enters the skin at the new position. If the angle is different than the initial angle at which the needle entered the skin, the tip of the needle can end up at the same point it was before the repositioning process began.

SUMMARY

The present invention is directed to methods and apparatuses for repositioning percutaneous probes. A method in accordance with one aspect of the invention includes engaging a housing coupled to the probe with a selected location on a skin surface, and inserting the probe through the skin at a first position on the surface of the skin, for example, relative to a target nerve region beneath the skin. The method can further include withdrawing the probe from the first position and reinserting the probe into the skin at a second position by moving the probe relative to the housing while the housing remains at the selected location. The method can still further include moving the probe in a first direction relative to the housing and away from the skin without moving the probe in a second direction relative to the housing and aligned with the skin. The probe can be moved relative to the housing by orbiting the probe about an axis offset from a central axis of the housing or by moving the probe along a straight line in a plane aligned with and offset from the surface of the skin.

A method in accordance with another aspect of the invention is directed to manufacturing a device for penetrating skin. The method can include fixedly positioning a probe in a slider member, disposing the slider member in a cavity of a housing, with the probe generally parallel to and offset from a major axis of the cavity, and at least restricting motion of the slider member out of the cavity by at least restricting rotational motion of the slider member in one direction relative to the housing. In a further aspect of the invention, the housing can include a first portion defining a first portion of the cavity and can be pivotably coupled to a second portion defining a second portion of the cavity. The method can further include positioning the slider member between the first and second portions of the housing and pivoting at least one of the first and second portions of the housing toward the other to receive a first part of the slider member in the first portion of the cavity and to receive a second part of the slider member in the second portion of the cavity.

The invention is also directed to an apparatus for piercing a skin surface. In one aspect of the invention, the apparatus can include a support housing having a casing defining an axial direction and an engaging surface to engage the skin surface at one end of the casing. The support housing can have a first guide extending axially away front the engaging surface and a second guide extending transverse to the first guide. The apparatus can further include a probe coupled to a guide member that is sequentially engaged with the first guide and the second guide to move in a first direction toward and away from the engaging surface without simultaneously moving in a second direction transverse to the first direction. In a further aspect of the invention, the first guide can include a first channel, the second guide can include a second channel, and the guide member can be slideably received. Sequentially in the first and second channels. The probe can be removably coupled to an, electrical contact, which is in turn connected to a current source for delivering percutaneous electrical stimulation to a recipient.

Figure 1:
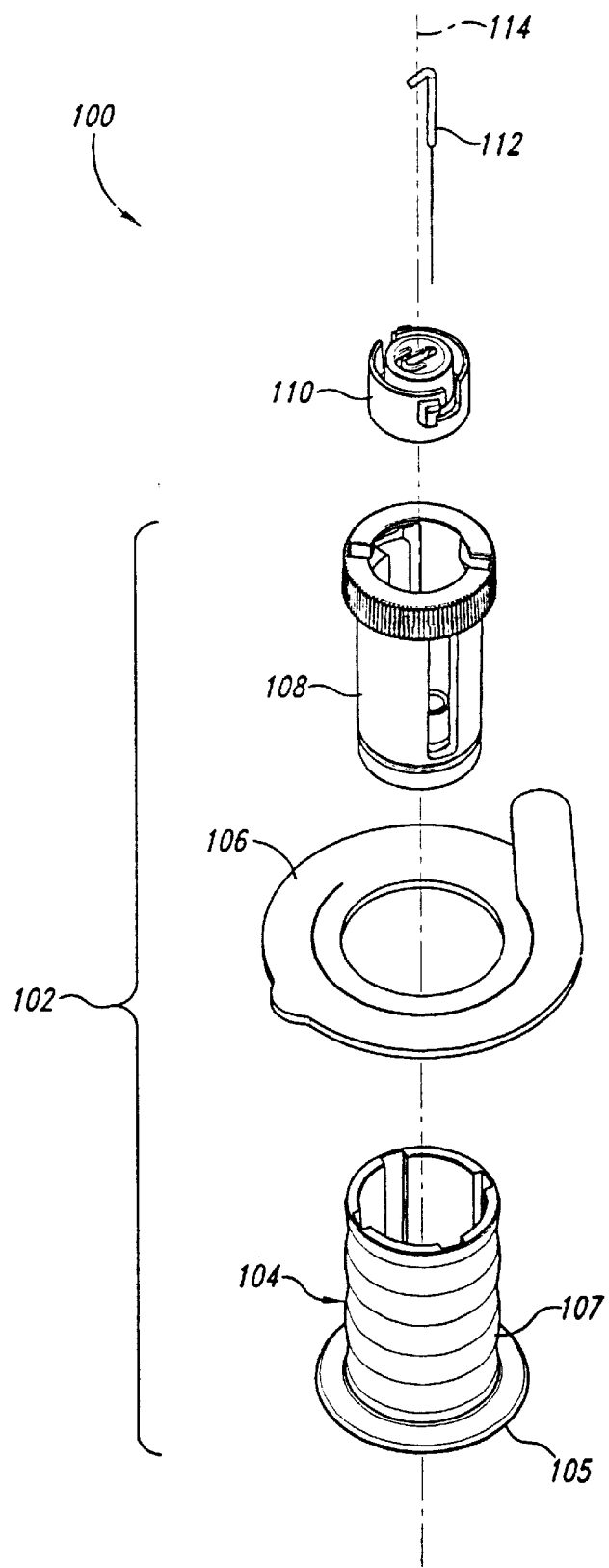
FIG. 1 is an exploded isometric view of a portion of a probe applicator in accordance with an embodiment of the invention.

In the drawings, identical references identity identical or substantially similar elements. To readily identity the discussion of any particular element, the most significant digit or digits in a reference number refer to the Figure number in which that element is first introduced (e.g., element 304 is first introduced and discussed in FIG. 3 and element 1504 is first introduced and discussed in FIG. 15).

DETAILED DESCRIPTION

Many specific details of certain embodiments of the invention are set forth in the following description and in FIGS. 1–15 to provide a thorough understanding of these embodiments. One skilled in the art, however, will understand that the present invention may have additional embodiments, or that the invention may be practiced without several of the details described below. Additionally, the following pending U.S. patent applications are incorporated herein in their entirety by reference: Ser. Nos. 09/452,477; 09/452,663; 09/452,508; 09/451,795; 09/451,799; 09/452,510; 09/451,800; 091451,796; 09/451,547; "Method and Apparatus for Electrically Coupling a Percutaneous Probe"; and "Percutaneous Probe Applicator".

The present invention describes methods and apparatuses for positioning probes, such as electrical therapy electrodes that deliver electrical current to a region of a patient's tissue by piercing the skin covering the tissue. The electrical current is generated by a control unit external to the patient and typically has particular waveform characteristics, such as frequency, amplitude and pulse width. Depending on the treatment or therapy being delivered, there may be one electrode containing both a cathode and an anode or a plurality of electrodes with at least one serving as a cathode and at least one serving as an anode.

The electrode has a sharp point to facilitate insertion through the patient's skin and to enhance local current density at a target site during treatment. The placement and location of the electrodes can be important for effective and efficient therapy. Accordingly, one aspect of the invention is directed toward a method and apparatus for repositioning a probe or electrode after an initial insertion.

FIG. 1 is an exploded top isometric view of probe applicator 100 that includes a housing 102 in accordance with an embodiment of the invention. The housing 102 can include a base 104 that rests on the patient's skin, an adhesive pad 106 to adhere the base 104 to the skin, and a sleeve 108 received in the base 104. The base 104 can include a skin engaging surface and a casing. For example, the skin engaging surface can be an annular lip 105 and the casing can be a tube 107 projecting from the lip 105 at a desired angle. A slider 110 fits in the sleeve 108 and supports a probe 112 for movement relative to the base 104. The probe 112 can include an electrode, a diagnostic probe, a drug delivery needle, a liquid extraction needle, or another transcutaneous or percutaneous device.

In operation, the slider 110 can slide downwardly and upwardly within the sleeve 108 to insert and retract the probe 112. The slider 110 and the sleeve 108 can rotate as a unit to selected positions relative to the base 104. In one aspect of this embodiment the slider 110, the sleeve 108, and the base 104 are all coaxial with a central axis 114 of the housing 102, and the probe 112 is offset or eccentric relative to the central axis 114. Accordingly, when the slider 110 and the sleeve 108 are rotated together as a unit relative to the base 104, the probe 112 orbits about the central axis 114 to a new position relative to the patient's skin surface.

Figure 2:
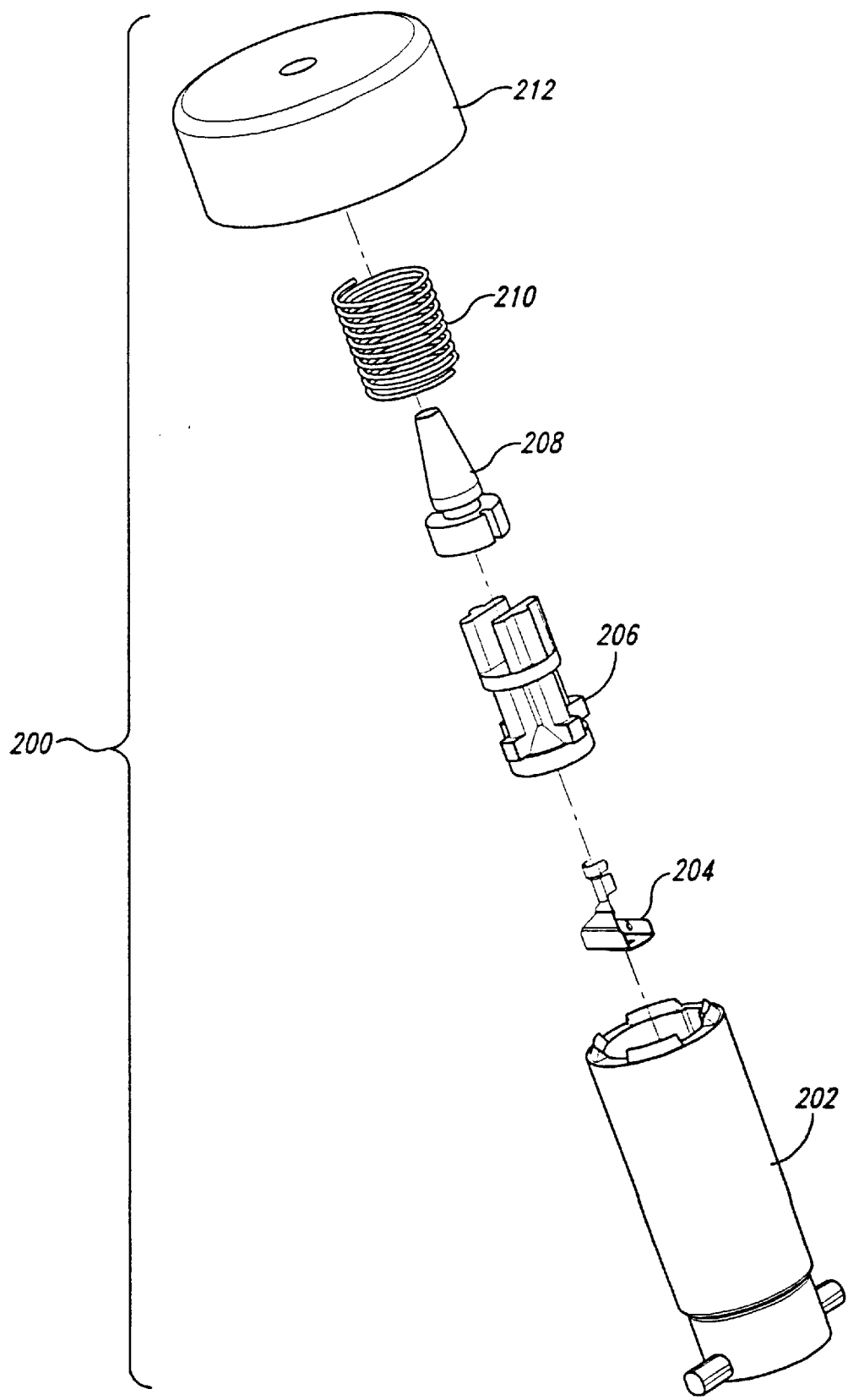
FIG. 2 is an exploded isometric view of an actuator that operates with the applicator shown in FIG. 1 in accordance with an embodiment of the invention.

FIG. 2 is an exploded top isometric view of an actuator 200 that engages the slider 110 (FIG. 1) and moves the slider 110 and the probe 112 (FIG. 1) in accordance with an embodiment of the invention. In one aspect of this embodiment, the actuator 200 can include a plunger 202 that releasably engages the slider 110 and translates the slider 110 axially within the sleeve 108 (FIG. 1). The actuator 200 can further include a contact plate 204 supported by a contact support 206 and biased against the probe 112 by a spring 210. A wire (not shown in FIG. 2) is connected to the contact 204 and passes through a grommet 208 and a cap 212 for coupling the contact 204 to a source of electrical power.

Figure 3:
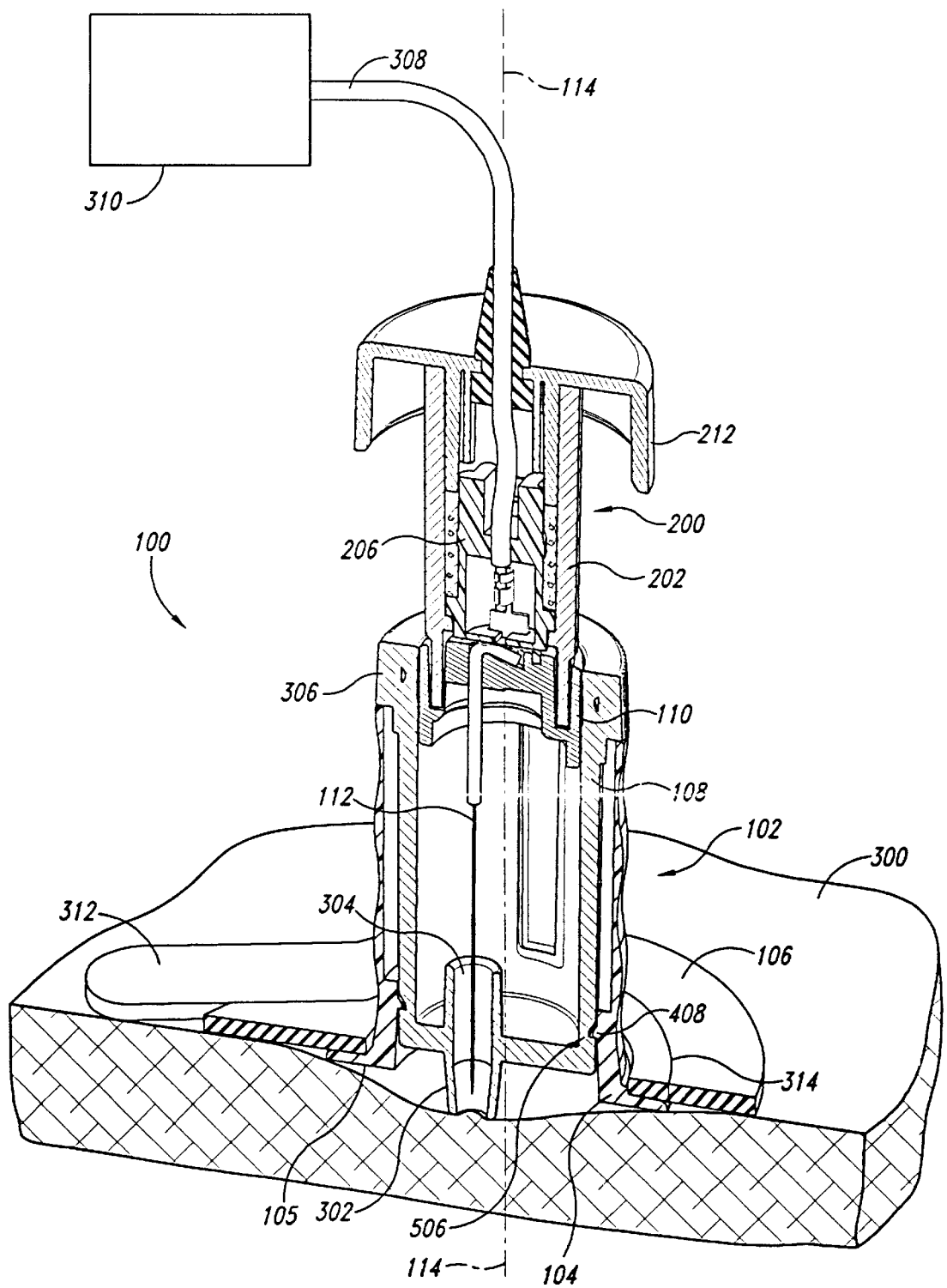
FIG. 3 is a partially schematic, cut-away side elevational view of the actuator shown in FIG. 2 coupled to the applicator shown in FIG. 1 and a power source in accordance with an embodiment of the invention.

FIG. 3 is a cut-away side isometric view of the apparatus 100 described above with reference to FIGS. 1 and 2 positioned on the surface of a patient's skin 300 in accordance with an embodiment of the invention. In one aspect of this embodiment, the base 104 has a flat lower surface and is releasably attached to the skin 300 with the adhesive pad 106. The base 104 is accordingly stably mounted to the skin 300, and the lip 105 of the base 104 is configured to direct the probe 112 at a right angle into the skin 300. The lip 105 of the base 104 can alternatively be configured to direct the probe 112 at another angle into the skin 300 in accordance with another embodiment of the invention. A probe tube 302 protrudes downwardly beneath the base 104 and includes a tube channel 304 through which the probe 112 passes. Accordingly, the probe tube 302 depresses and stretches the skin 300 beneath the base 104, while allowing the skin 300 to bulge upwardly slightly within the tube channel 304. As a result, the patient may be less aware of and/or less alarmed by the passage of the probe 112 into the skin 300, The probe 112 is inserted into the skin 300 by grasping the cap 212 of the actuator 200 and depressing the plunger 202 until the slider 110 contacts the top of the probe tube 302. If the probe 112 is to be repositioned in the skin 300, the plunger 202 is raised until the slider 110 is aligned with a sleeve rim 306 of the sleeve 108, as shown in FIG. 3. The practitioner then grasps the sleeve rim 306 and rotates the sleeve 108, the slider 110 and the plunger 202 about the central axis 114 within the base 104 to a new position relative to the skin surface 300. As the slider 110 rotates about the axis 114, the eccentric probe 112 and the probe tube 302 orbit about the axis 114 to the new position. Once the sleeve 108 is in the new position, the practitioner depresses the plunger 202 to reinsert the probe 112 in the new position.

When the probe 112 includes an electrode for percutaneous electrical nerve stimulation, the practitioner then couples an electrical lead 308 between the probe 112 and a control unit 310 that supplies electrical power to the probe 112. In one embodiment, the control unit 310 supplies a current-regulated and current-balanced waveform with an amplitude of up to 20 milliamps, a frequency of from approximately 4 Hz to approximately 5 Hz, and a pulse width of from approximately 50 microseconds to approximately 1 millisecond. In other embodiments, the control unit 310 can supply other waveforms having other characteristics. In still further embodiments, the control unit 310 can control the voltage applied to the probe 112 in addition to or in lieu of controlling the current.

In one embodiment the housing 102 remains in place on the patient's skin 300 throughout the treatment, which can last 30 minutes in one aspect of this embodiment. When the treatment is complete, the housing 102 may be removed by first retracting the probe 112 from the skin 300, following the steps described above in reverse order. The housing 102 can then be lifted from the skin 300 after releasing the adhesive pad 106 from the skin 300. In one aspect of this embodiment, the adhesive pad 106 can include a non-adhesive tab portion 312 and a perforated slit 314 to facilitate removing the adhesive pad 106. A new housing 102 can be attached to the patient for each subsequent treatment. Alternatively, the housing 102 can remain attached to the patient for more than one treatment session.

Figure 4:
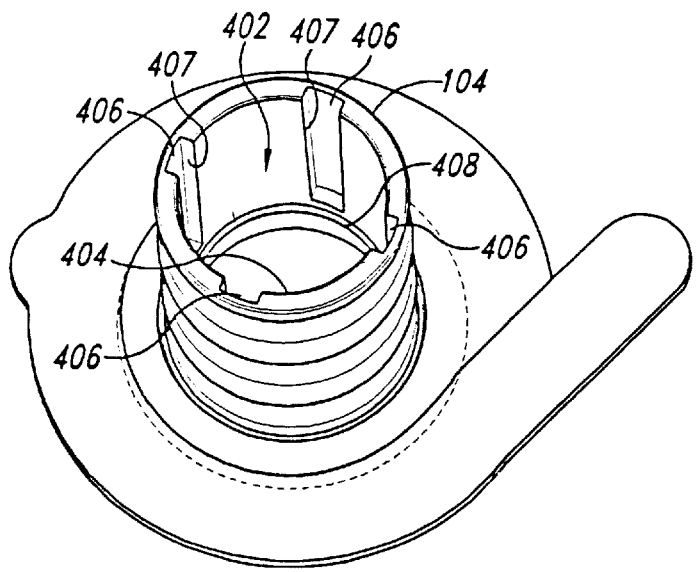
FIG. 4 is a top isometric view of a base of an applicator in accordance with an embodiment of the invention.
Figure 5:
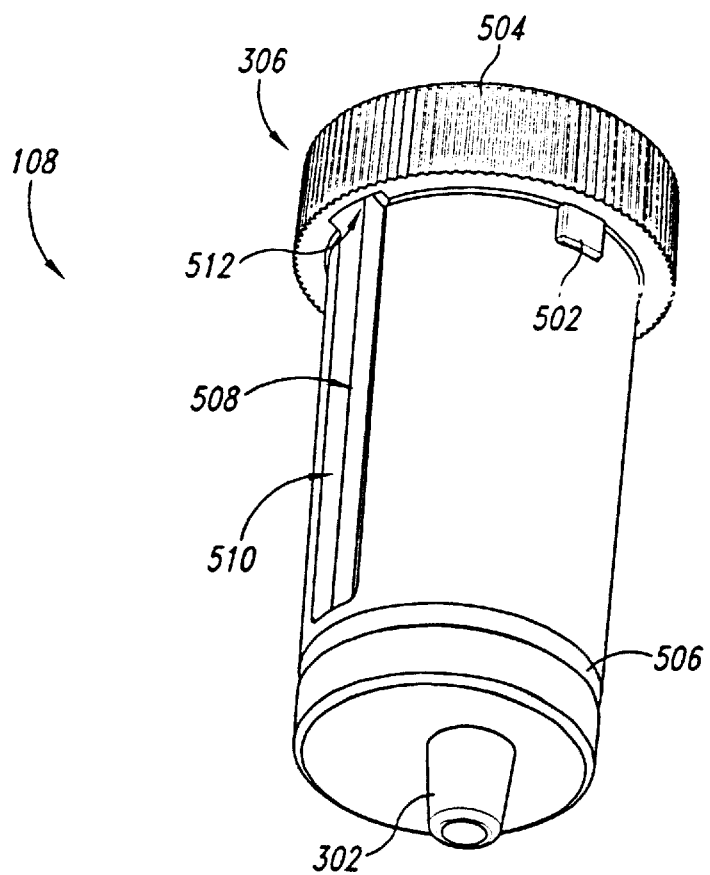
FIG. 5 is a bottom isometric view of an applicator sleeve in accordance with an embodiment of the invention.

FIG. 4 is a top isometric view of an embodiment of the base 104 shown in FIGS. 1 and 3. FIG. 5 is a bottom isometric view of an embodiment of the sleeve 108 shown in FIGS. 2 and 3. Referring now to FIGS. 4 and 5, the base 104 can include a hollow receiving cylinder 402 sized to rotatably receive the sleeve 108. The receiving cylinder 402 can have an inner surface 404 with a plurality of axial base channels 406 defined by channel walls 407 and sized to receive corresponding sleeve locator tabs 502 of the sleeve 108. In one aspect of this embodiment, the sleeve 108 can include two oppositely facing sleeve locator tabs 502 (one of which is visible in FIG. 5) and the base 104 can include two pairs of oppositely facing axial channels 406. In other embodiments, the sleeve 108 can have a different number of sleeve locator tabs 502, and/or the base 104 can have a different number of axial base channels 406. In either embodiment the practitioner ran rotate the sleeve 108 relative to the base 104 by grasping finger grips 504 disposed around the sleeve rim 306 and twisting the sleeve 108 clockwise or counterclockwise to force the sleeve locator tabs 502 out of one pair of axial base channels 406 and into the next pair of axial base channels 406.

In one aspect of an embodiment shown in FIGS. 4 and 5, the practitioner is at least restricted from (or prevented from) moving the sleeve 108 axially relative to the base 104 by a retaining lip 408 in the base 104 that projects radially inwardly from the inner surface 404 and is received in a corresponding retaining groove 506 in the sleeve 108. The retaining lip 408 can have a downwardly tapered side surface that snaps into the retaining groove 506 when the sleeve 108 is initially inserted into the base 104 during installation. The retaining lip 408 can also have a downwardly facing step surface that engages a corresponding upwardly facing surface of the retaining groove 506 to prevent further axial movement of the sleeve 108 relative to the base 104, while allowing rotational movement of the sleeve 108 relative to the base 104 (as is also shown in FIG. 3).

In one embodiment, the sleeve 108 has two sleeve axial guide channels 508 that align with a corresponding pair of the axial base channels 406 in the base 104 when the sleeve tabs 502 are positioned in the other pair of axial base channels 406. Each sleeve axial guide channel 508 includes a lower portion 510 that is coextensive with one of the axial base channels 406 and an upper portion 512 in the rim 306 above the axial base channels 406. This arrangement can prevent the practitioner from simultaneously moving the probe 112 (FIG. 3) axially and transversely relative to the patient's skin 300 (FIG. 3). As described below with reference to FIG. 6, this arrangement can also prevent the practitioner from moving the probe 112 transversely relative to the skin 300 until the probe 112 is fully retracted from the skin 300.

Figure 6:
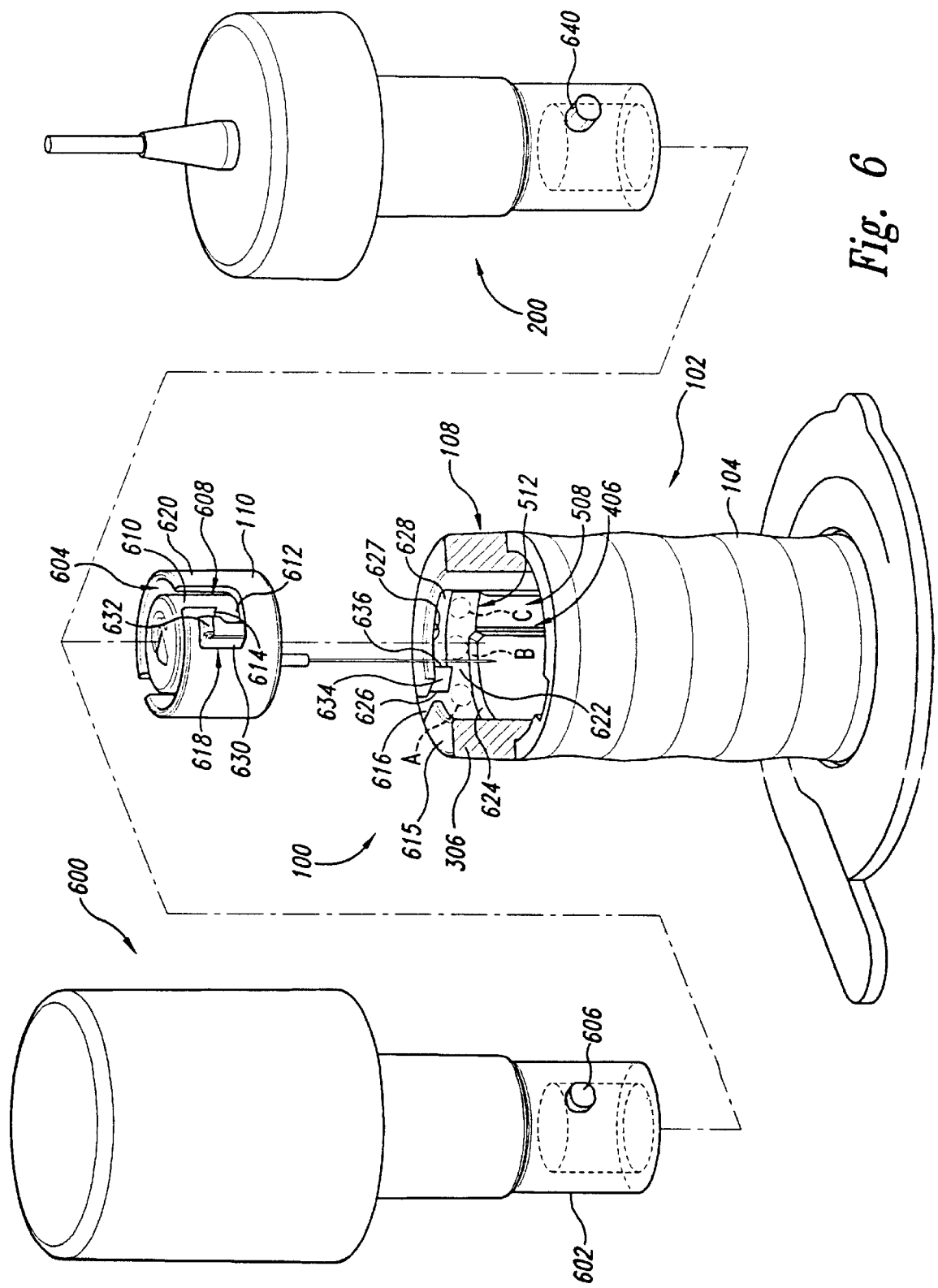
FIG. 6 is an exploded side isometric view of a slider, an assembly tool, and an actuator positioned adjacent to an applicator base in accordance with an embodiment of the invention.

FIG. 6 is a top isometric view of the slider 110 positioned above the sleeve 108, which has been inserted into the base 104 of the applicator 100 in accordance with an embodiment of the invention. In one aspect of this embodiment, the slider 110 is installed in the housing 102 during assembly by operating an assembly tool 600. Once installed, the slider 110 can be moved relative to the housing 102 by the practitioner, who can engage the slider 110 with the actuator 200. The operations of the assembly tool 600 and the actuator 200 are described in turn below. Further details of an overall process for assembling the applicator 100 are described below with reference to FIGS. 8–12.

In one embodiment, the assembly tool 600 includes a thin-walled cylinder 602 that is removably received in a corresponding circular groove 604 in the slider 110. The assembly tool 600 can also include two assembly pegs 606 (one of which is visible in FIG. 6) that are received in corresponding peg channels 608 of the slider 110. Each peg channel 608 can include an axial portion 610 and a transverse portion 612. The transverse portion 612 can have a curved upper surface 614 shaped to receive the assembly peg 606. To engage the assembly tool 600 with the slider 110, the installer aligns the assembly pegs 606 of the assembly tool 600 with the axial portions 610 of the peg channels 608. The installer then lowers the assembly tool 600 into the circular groove 604 of the slider 110. When the assembly pegs 606 reach the bottom of the axial portions 610 of the peg channels 608, the installer rotates the assembly tool 600 clockwise until the assembly pegs 606 reach the clockwise ends of the transverse portions 612 of the peg channels 608. The installer can then release downward pressure on the assembly tool 600 to allow the spring 210 (FIG. 3) to bias the assembly pegs 606 upwardly against the upper surface 614 of the peg channels 608 and retain the slider 110 in engagement with the tool 600. In one aspect of this embodiment, each assembly peg 606 is flush with or recessed from an outer surface 620 of the slider 110 so as not to interfere with the motion of the slider 110 into the sleeve 108, as described below, In one embodiment, the slider 110 includes two guide members 618 (one of which is visible in FIG. 6). The rim 306 of the sleeve 108 has a flat, transverse lip 615 with oppositely facing apertures 616 (one of which is visible in FIG. 6), each sized to receive one of the guide members 618. In one aspect of this embodiment, one guide member 618 can be larger than the other, and one aperture 616 can be larger than the other so that the slider 110 can be inserted into the sleeve 108 in only one orientation. Accordingly, the probe 112 will automatically align with the probe tube 302 (FIG. 3). Alternatively, both guide members 618 can have approximately the same size. In either embodiment, the assembly tool 600 and the slider 110 are both lowered as a unit toward the housing 102 until the guide members 618 are received in the apertures 616 of the rim 306, The rim 306 of the sleeve 108 can have transverse guide channels 622 that extend between each of the apertures 616 and a corresponding upper portion 512 of one of the sleeve axial guide channels 508. Each transverse guide channel 622 is defined in part by a channel floor 624 and includes a rotational stop 626 to restrict counterclockwise rotation of the slider 110. The transverse guide channel 622 can further include a sleeve rotational restriction 627 that extends axially downwardly from the lip 306 into the transverse guide channel 622 to restrict rotational motion of the slider 110. A sleeve axial restriction 628 is offset axially downwardly from the rim 615 and can extend radially inwardly to engage the guide members 618 and restrict axial motion of the slider 110. Accordingly, the sleeve rotational restriction 627 cooperates with a slider rotational restriction 630 of the slider 110, and the sleeve axial restriction 628 cooperates with a slider axial restriction 632 of the slider 110, as described in greater detail below.

When the slider 110 and the assembly tool 600 are lowered into the apertures 616, the assembly pegs 606 are received in the transverse guide channels 622 of the sleeve rim 306, with one of the assembly pegs 606 at position "A" (indicated by dashed lines in FIG. 6). The guide members 618 are also positioned in the transverse guide channel 622 adjacent to the assembly, pegs 606. When the installer rotates the assembly tool 600 clockwise, the slider rotational restriction 630 passes over an inclined ramp surface 634 of the rotational stop 626 and then snaps into place against the sleeve rotational restriction 628. The assembly pegs 606 are now at position "B," and the axial portions 610 of the peg channels 608 in the slider 110 are aligned with the apertures 616. Because a rear surface 636 of the rotational stop 626 is flat and directly faces the slider rotational restriction 630, the slider 110 is prevented from rotating counterclockwise past the rotational stop 626. At this point, the slider rotational restriction 630 engages the sleeve rotational restriction 626 and the slider axial restriction 632 rides along the upper surface of the sleeve axial restriction 628 just beneath the rim 615. The slider 110 is now installed in the housing 102 and the assembly tool 600 is removed by depressing the tool 600 slightly to disengage the assembly pegs 606 from the upper surfaces 614 of the peg channels 608. The installer then rotates the assembly tool 600 counterclockwise until the assembly pegs 606 are aligned with the axial portions 610 of tile peg channels 608 at position "A", and lifts the assembly tool 600 clear of the slider 110 and the housing 102. In one aspect of this embodiment, the housing 102 with the slider 110 installed can now be provided to an end user or practitioner along with a separate actuator 200.

To operate the probe applicator 100, the practitioner attaches the applicator 100 to the patient's skin 300, as described above with reference to FIG. 3. The practitioner then engages the actuator 200 shown in FIG. 6 with the slider 110 by aligning actuator pegs 640 with the apertures 616 in the rim 306 of the housing 102, and lowering the actuator pegs 640 into the apertures 616. The practitioner rotates the actuator 200 until the actuator pegs 640 engage the slider 110. At this point, one of the actuator pegs 640 is located at position "B" in the transverse guide channel 622. The practitioner then continues to rotate the actuator 200 clockwise, forcing each guide member 618 past the corresponding sleeve rotational restriction 627 until the one actuator peg 640 is at position "C." At this point, the guide members 618 and the actuator pegs 640 are aligned with the upper portion 512 of the sleeve axial guide channel 508 and the base axial channel 406. When the slider rotational restriction 630 of guide member 618 "clicks" past the sleeve rotational restriction 627, the practitioner receives mechanical and/or audio feedback indicating that the slider 110 has the proper rotational position for inserting the probe 112 into the patient.

To insert the probe 112 into the patient, the practitioner exerts a downward force on the actuator 200, forcing the slider axial restrictions 632 over the sleeve axial restrictions 628 until the slider axial restriction 632 "clicks" over the sleeve axial restriction 628, giving the practitioner additional mechanical feedback indicating that the slider 110 is correctly positioned for continued insertion. The practitioner then depresses the actuator 200, forcing the slider 110 downwardly through the sleeve 108 with less mechanical resistance than was required to snap the slider axial restrictions 632 over the sleeve axial restrictions 628. The downward movement of the slider 110 through the sleeve 108 moves the probe 112 downwardly through the probe tube 302. In one aspect of this embodiment, the weight of the slider 110 is sufficient to cause it to descend freely downwardly, and the only force exerted by the practitioner is the force necessary to insert the probe 112 into the patient. As the slider 110 moves downwardly, the sleeve axial guide channels 508 guide the guide members 618 along an axial path, and the base axial channels 406 receive and guide the actuator pegs 640 along a parallel axial path.

If the probe 112 is to be repositioned, the practitioner moves the actuator 200) and the slider 110 upwardly, with the sleeve axial guide channels 509 guiding the guide members 618 and the base axial channels 406 guiding the actuator pegs 640 to ensure that the motion of the probe 112 is moved only in the axial direction. If the practitioner attempts to rotate the rim 306 before the slider 110 has been fully retracted so that the slider axial restrictions 632 snap into position above the sleeve axial restrictions 628, the actuator pegs 640 will bear against the channel walls 407 (FIG. 4) of the base axial channel 406, preventing such rotation. The practitioner continues to raise the actuator 200 and the slider 110 until the slider axial restrictions 632 snap back over the sleeve axial restrictions 628 to ensure that the one actuator peg 640 is located in the transverse guide channel 622 at position "C." At this point, the probe 112 has been completely retracted from the skin 300 (FIG. 3) and the sleeve axial restrictions 628 can keep the slider 110 and the probe 112 from sliding downwardly until the practitioner is ready to re-insert the probe 112. The practitioner then rotates the slider 110, the probe 112, the actuator 200 and file sleeve 108 as a unit by grasping the rim 306 of the sleeve 108 and rotating the rim 306 relative to the base 104, as described above with reference to FIG. 3. Once the probe 112 has been rotated to the new position, the practitioner re-inserts the probe 112. Accordingly, the sleeve axial channels 508, the base axial channels 406, and the transverse channels 622 of the rim 306 sequentially guide the probe 112 axially and transversely relative to the skin 300.

One feature of an embodiment of the probe applicator 100 described above with reference to FIGS. 1–6 is that the arrangement of the housing 102, the slider 110 and the actuator 200 allows the practitioner to reposition the probe 112 transversely relative to the patient's skin (by orbiting the probe 112 about the central axis 114), and allows the practitioner from moving the probe 112 axially (for probe insertion and retraction), but prevents the practitioner from moving the probe 112 transversely until the probe 112 is completely removed from the patient. An advantage of this feature is that the practitioner will be less likely to harm the patient by moving the probe 112 transversely while the probe 112 is still inserted in the patient.

Another advantage of an embodiment of the applicator 100 described above with reference to FIGS. 1–6 is that the practitioner can reposition the probe 112 relative to the patient's skin 300 without disengaging the entire housing 102 from the patient. For example, when the probe 112 is an electrical stimulation needle, the practitioner can fasten the housing 102 to the skin 300 above the general location of the nerve region that is to receive electrical stimulation and then fine-tune the location by rotating the probe 112 relative to the housing 102 while the housing 102 remains attached to the patient's skin 300. In one embodiment, the probe 112 can be offset from the central axis 114 by a distance of 0.090 inches, and can be positioned in one of four preselected positions, with each preselected position being approximately 0.127 inches from an adjacent position. In other embodiments, the probe 112 can be moved to more or fewer preselected positions, and the preselected positions can be separated by greater or lesser distances.

Figure 7:
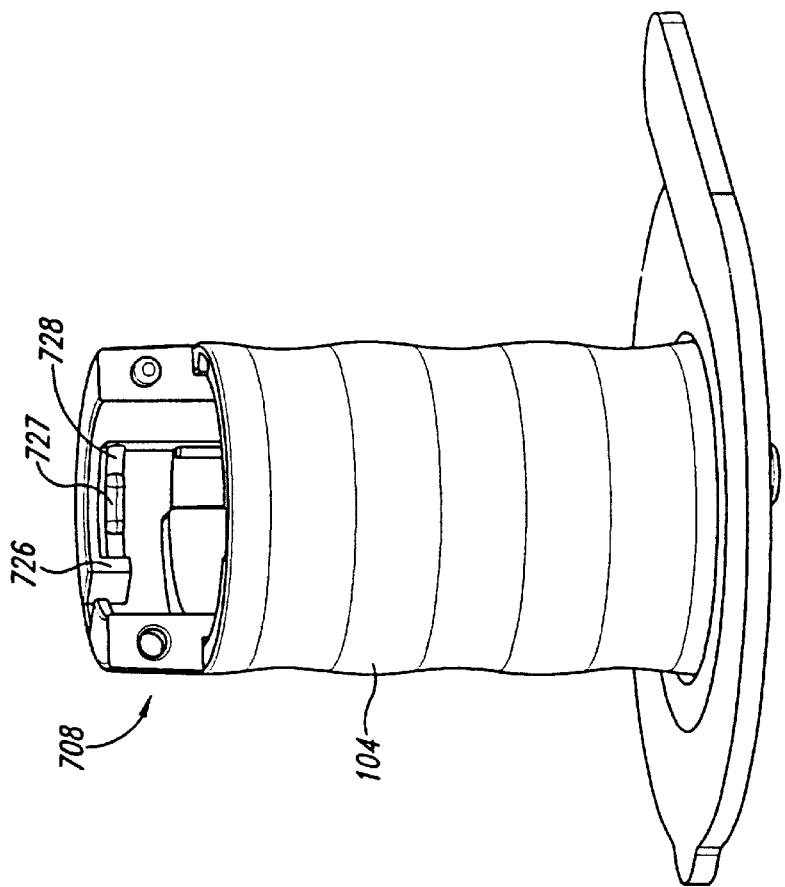
FIG. 7 is a partially cut-away side isometric view of a base and a sleeve configured in accordance with another embodiment of the invention.

FIG. 7 is a partially cut-away side isometric view of a sleeve 708 installed in the base 104 in accordance with another embodiment of the invention. In one aspect of this embodiment, the sleeve 708 includes a rotation stop 726 that does not have an inclined surface 634 (FIG. 6). Accordingly, the slider 110 (FIG. 6) is positioned in the sleeve 708 before the sleeve 708 is installed in the base 104, as will be described in greater detail below with reference to FIG. 9. In another aspect of this embodiment, the sleeve 708 includes a sleeve rotational restriction 727 that is integrated with a sleeve axial restriction 728. Accordingly, the sleeve rotational restriction 727 can project radially inward from the sleeve axial restriction 728. The sleeve rotational restriction 727 and axial restriction 728 cooperate with the slider rotational restriction 630 (FIG. 6) and the slider axial restriction 632 (FIG. 6) in a manner generally similar to that described above with reference to FIG. 6 to restrict rotational and axial motion, respectively, of the slider 110.

FIGS. 8–12 illustrate a process for assembling a probe applicator 100 in accordance with an embodiment of the invention. Many of the non-conductive components of the applicator 100 (such as the sleeve 108) can be formed from a high-density polyethylene. The base 104 and the slider 10 can be formed from materials having surface characteristics that promote or at least do not inhibit relative motion between the sleeve 108 and the base 104, and between the slider 110 and the sleeve 108. Such materials include high impact polystyrenes. These components can be injection molded or otherwise pre-formed in preparation for assembly.

Figure 8:
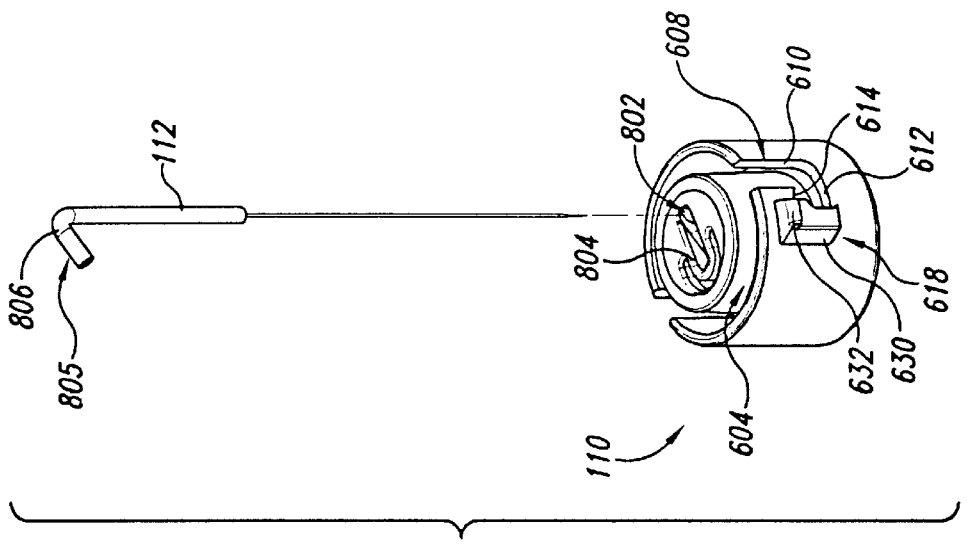
FIG. 8 is a top isometric view of probe positioned above a slider for assembly in accordance with an embodiment of the invention.

Beginning with FIG. 8, the probe 112 is positioned above a probe aperture 802 in the slider 110 and lowered into the aperture 102. In one aspect of this embodiment, a semicircular retaining ridge 804 is then swaged or otherwise deformed over the top of an end 805 of the probe 112, leaving an elbow portion 806 of the probe 112 exposed. Alternatively, an initially separate plastic piece can be bonded to the slider 110 over the top end 805 of the probe 112 to secure the probe 112 in position. Accordingly, the probe 112 can be secured in the slider 110, while the electrically conductive elbow portion 806 of the probe 112 remains exposed for engaging the contact plate 204 (FIG. 2) to electrically couple the probe 112 to the control unit 310 (FIG. 3).

Figure 9:
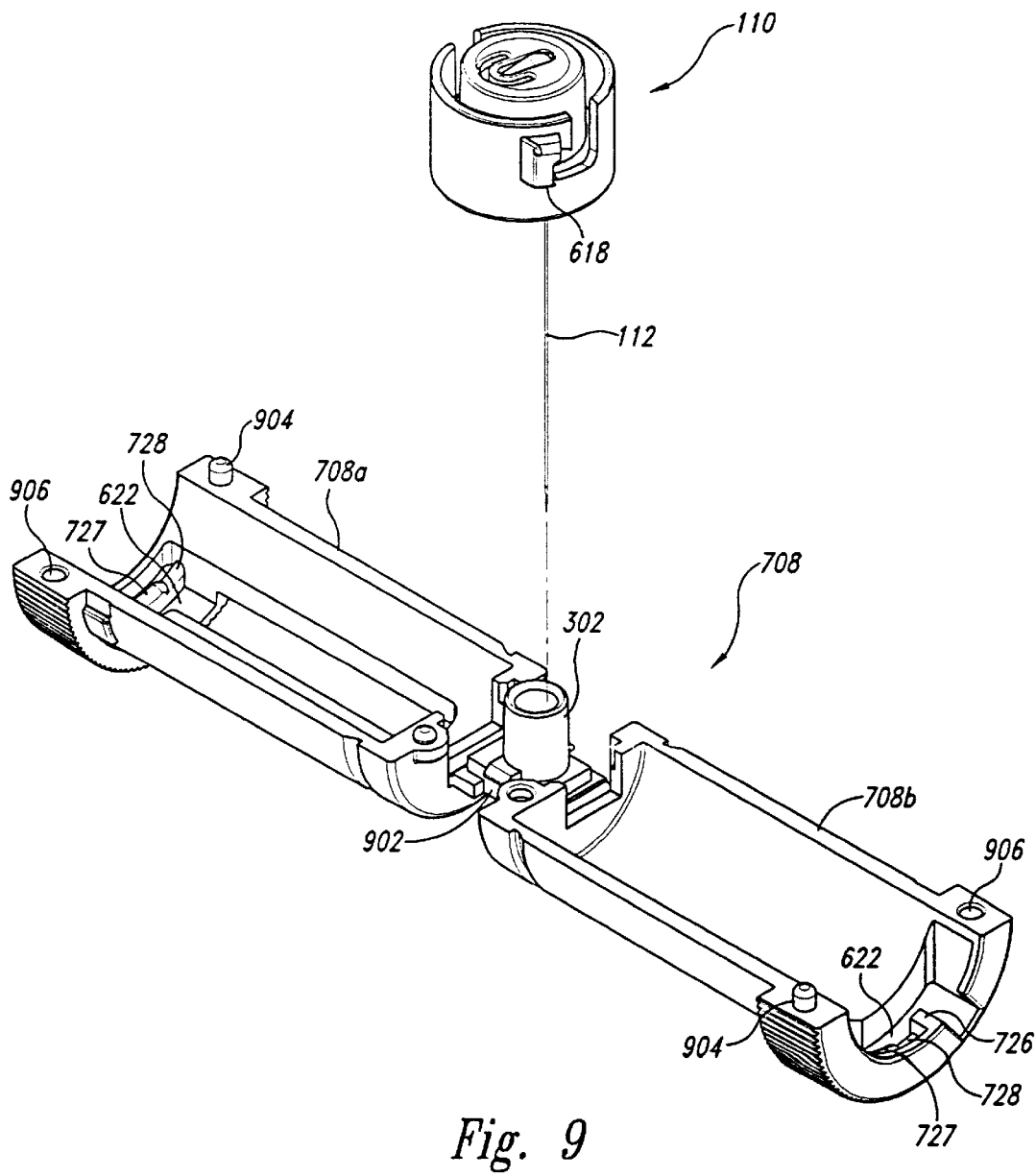
FIG. 9 is a top isometric view of the slider and the probe of FIG. 8 positioned above a sleeve for assembly in accordance with an embodiment of the invention.

FIG. 9 illustrates a process for installing the slider 110 and the probe 112 into a sleeve 708 of the type described above with reference to FIG. 7. In one embodiment, the sleeve 708 can include two sleeve halves 708a, 708b, each pivotably corrected to a central portion 902 that also supports the probe tube 302. The slider 110 is positioned relative to the sleeve halves 708a, 708b with the probe 112 aligned with the probe tube 302. The sleeve halves 708a, 708b are then pivoted upwardly around the slider 110 until alignment pegs 904 on each sleeve half enter opposing alignment apertures 906 of the other sleeve half. As the sleeve halves 708a, 708b close around the slider 110, the guide members 618 of the slider 110 are received in the transverse guide channels 622 of the sleeve 708. Each guide member 618 is positioned in the corresponding transverse guide channel 622 at an angular location between the corresponding sleeve rotation restriction 727 and the rotation stop 726, with the guide members 618 engaged with the sleeve axial restrictions 728. Accordingly, the slider 110 cannot be rotated counterclockwise past the rotation stops 726.

Figure 10:
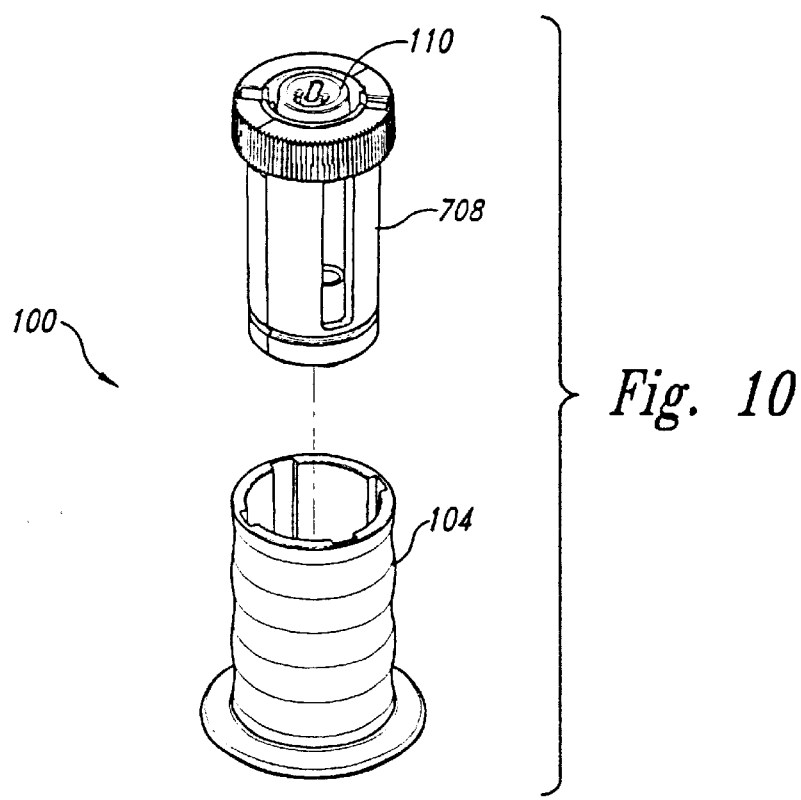
FIG. 10 is a top isometric view of a slider installed in a sleeve and positioned above a base for assembly in accordance with an embodiment of the invention.
Figure 11:
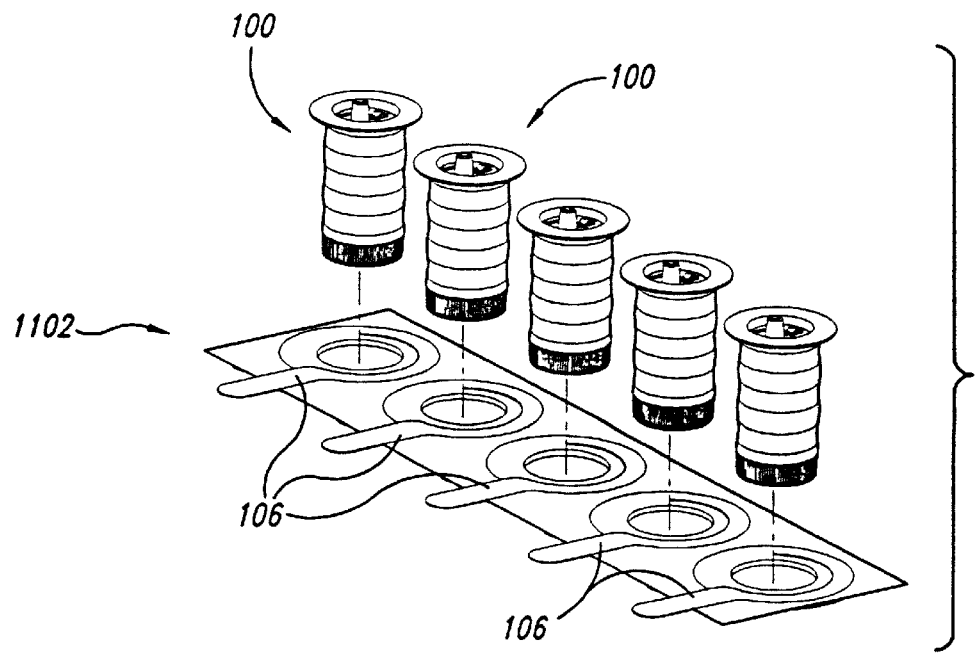
FIG. 11 is a top isometric view of a plurality of bases positioned above a plurality of adhesive pads for assembly in accordance with an embodiment of the invention.
Figure 12:
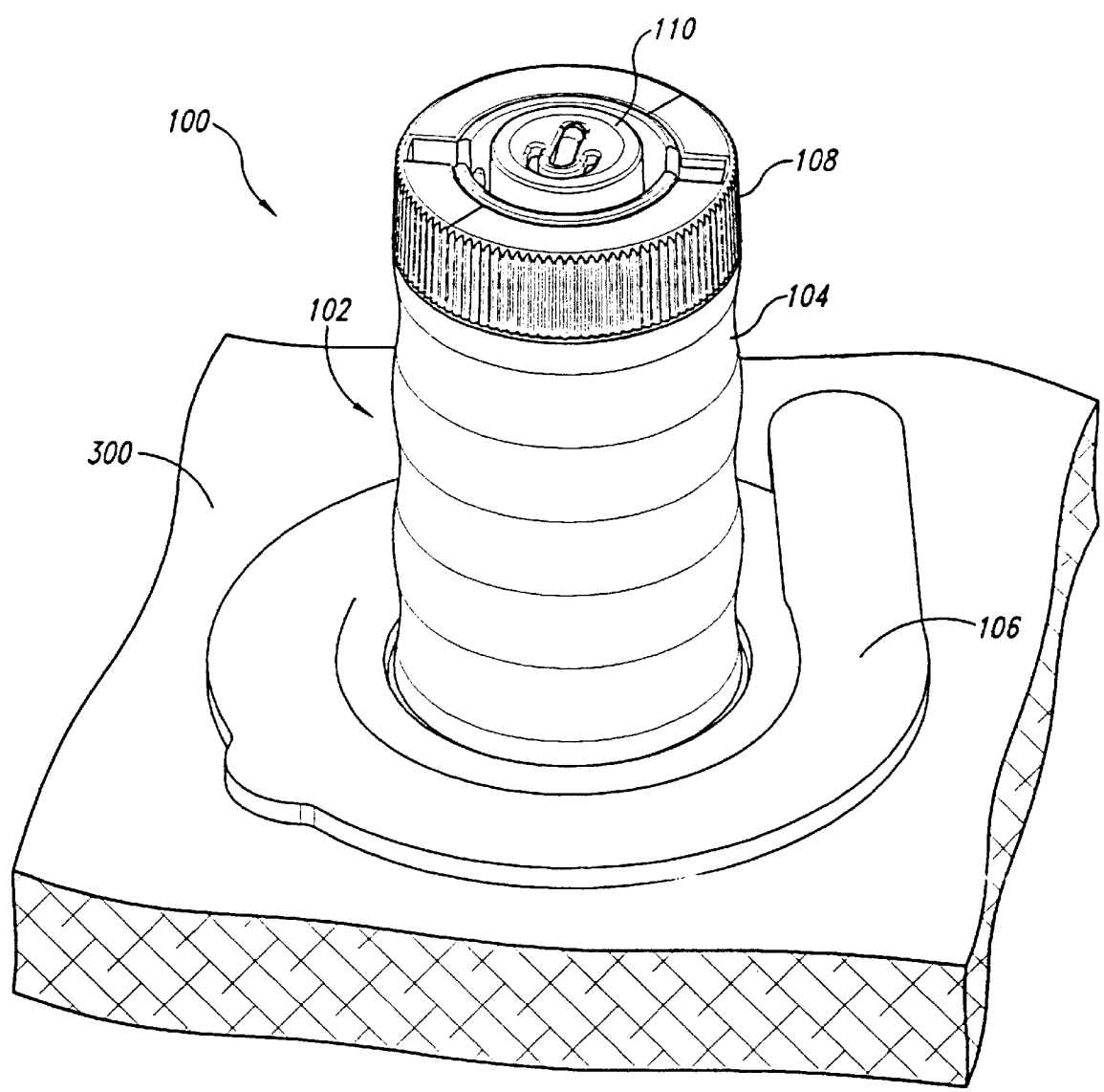
FIG. 12 is a top isometric view of an assembled applicator in accordance with an embodiment of the invention.

As shown in FIG. 10, the sleeve 708 (or, alternatively, the sleeve 108) is lowered into the base 104 (with the slider 110 pre-installed in the sleeve 708) to form the applicator 100. Referring now to FIG. 11, a plurality of the applicators 100 (each without an actuator 200) can be attached to a strip 1102 that has a corresponding plurality of adhesive pads 106. The strip 1102 with the applicators 100 attached can then be packaged for shipment. When the practitioner is ready to attach the applicator 100 to a patient, the practitioner removes an individual applicator 100 and adhesive pad 106 from the strip 1102 and inverts the applicator 100 for attachment to the patient's skin, as shown in FIG. 12. The practitioner then operates the applicator 100 with the actuator 200, as described above.

One feature of an embodiment of the applicator 100 described above is that the actuator 200 is removable from the housing 102 and is reusable with other applicators 100. Accordingly, the practitioner can use a single actuator 200 to operate a plurality of applicators 100. An advantage of this arrangement is that it can reduce the practitioner's costs because the practitioner need not purchase a new actuator 200 with each applicator 100.

Figure 13A:
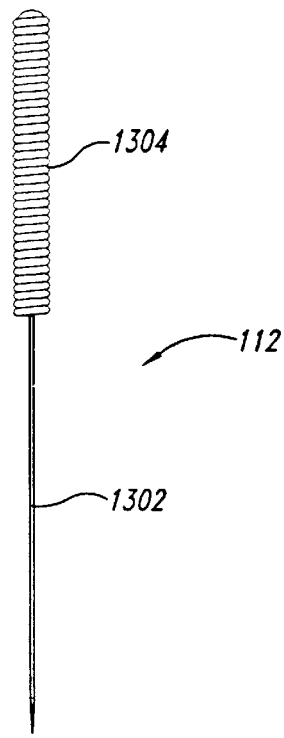
FIGS. 13A–C illustrate probes in accordance with further embodiments of the invention.
Figure 13B:
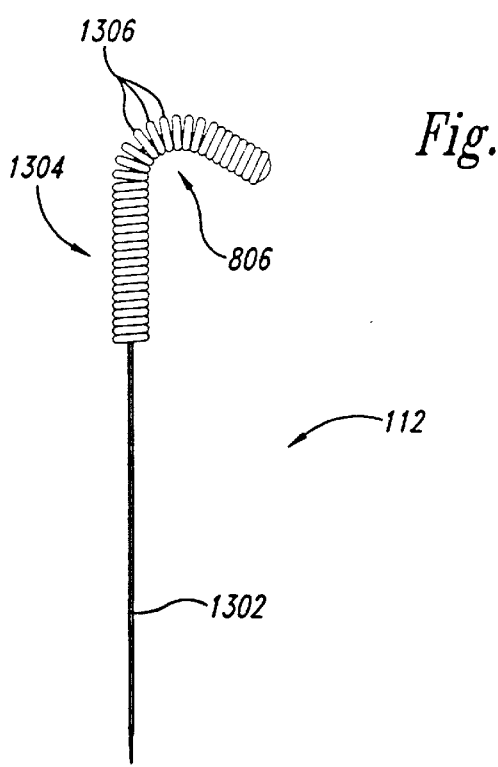
Figure 13C:
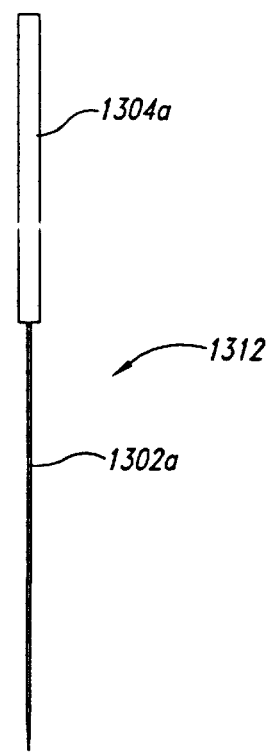

FIG. 13A is a side elevational view of an embodiment of the probe 112 described above with reference to FIG. 1. In one aspect of this embodiment, the probe 112 can include a standard 3 cm long acupuncture needle having a shaft 1302 and a handle 1304 formed from a coiled, electrically conductive material such as 32-gauge stainless steel wire. As shown in FIG. 13B, the probe 112 can be bent to form the elbow portion 806 described above with reference to FIG. 8. The wire that forms the handle 1304 tends to separate at the elbow portion 806 to form individual spaced-apart coil sections 1306. One or more of the coiled sections 1306 engage the contact plate 204 (FIG. 2) to provide an electrical connection to the control unit 310 (FIG. 3). In an alternative embodiment shown in FIG. 13C, a probe 1312 can include a shaft 1302a integrally formed with a solid handle 1304a. The handle 1304a can be bent to form a solid elbow portion having an overall shape generally similar to that described above with reference to FIG. 13B. The probes 112, 1312 can have other configurations in other embodiments (for example, the probes can include sharpened lengths of wire), so long as the probes are compatible with the applicator 100 and the shafts 1302, 1302a can operate percutaneously.

Figure 14:
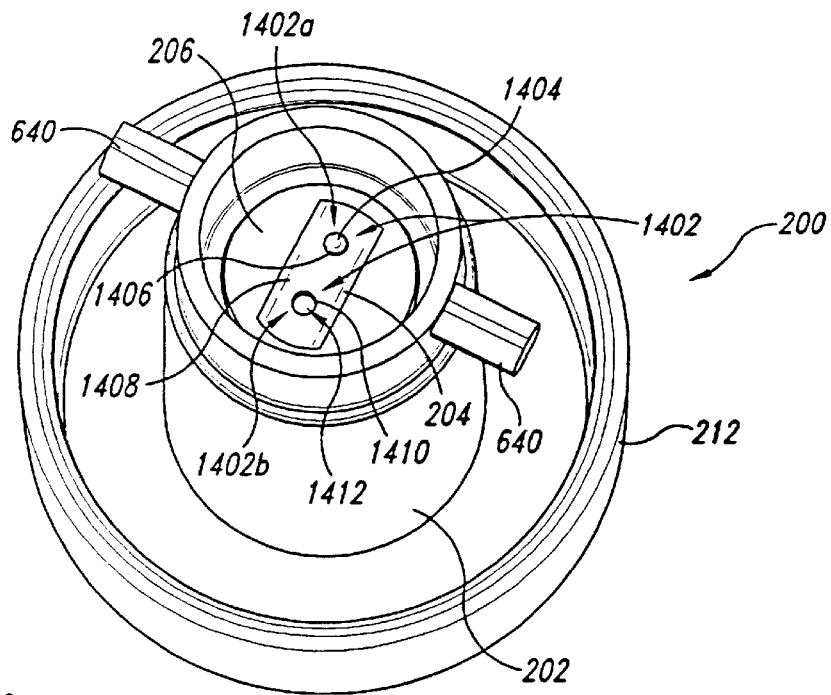
FIG. 14 is a bottom isometric view of a plunger having electrical contacts in accordance with an embodiment of the invention.

FIG. 14 is a bottom isometric view of an embodiment of the actuator 200 described above with reference to FIGS. 2 and 6 having contact features 1402 in the contact plate 204 for engaging the probe 112 (FIG. 1). In one aspect of this embodiment, the contact plate 204 of the actuator 200 can include two contact features 1402, shown as a first contact feature 1402a and a second contact feature 1402b. The contact features 1402a and 1402b can have identical configurations or, (as shown in FIG. 14) each contact feature 1402a and 1402b can have a different configuration. The contact plate 204 can have two contact features 1402, for example, when there are two possible orientations with which the actuator 200 can engage the slider 110 (FIG. 6). Alternatively, the contact plate 204 can have more or fewer contact features 1402 in other embodiments.

In one embodiment, the first contact feature 1402a can have a circular convex dimple shape with a first portion 1404 facing outwardly opposite a second portion 1406. Accordingly, when the actuator 200 is rotated into engagement with the slider 110, the contact feature 1402a can ride over the probe 112 so that initially the first portion 1404 engages the probe 112, and then the second portion 1406 engages the probe 112.

In a further aspect of this embodiment, the first contact feature 1402a can provide a mechanical feedback to the user to indicate when positive contact has been established between the first contact feature 1402a and the probe 112. For example, referring now to FIGS. 6, 8 and 14, the first contact feature 1402a can ride up over the elbow portion 806 of the probe 112, as the actuator 200 is rotated from position "A" to position "B." As the first contact feature 1402a passes over the probe 112, the user can feel the first contact feature 1402a "click" into place, providing feedback that the first contact feature 1402a has properly engaged the probe 112.

The second contact feature 1402b can operate in a manner generally similar to that discussed above with reference to the first contact feature 1402a, but instead, the second contact feature 1402b can be recessed from a surface 1408 of the contact 204. For example, the second contact feature 1402b can include a concave dimple or an aperture. In either aspect of this embodiment, the second contact feature 1402b can have an edge 1410 that slides over the elbow portion 806 of the probe 112 so that the elbow portion 806 is received in a concave region 1412 of the second contact feature 1402b. Accordingly, the second contact feature 1402b can also provide mechanical feedback to the user, indicating when the contact feature 1402b is properly engaged with the probe 112.

Figure 15:
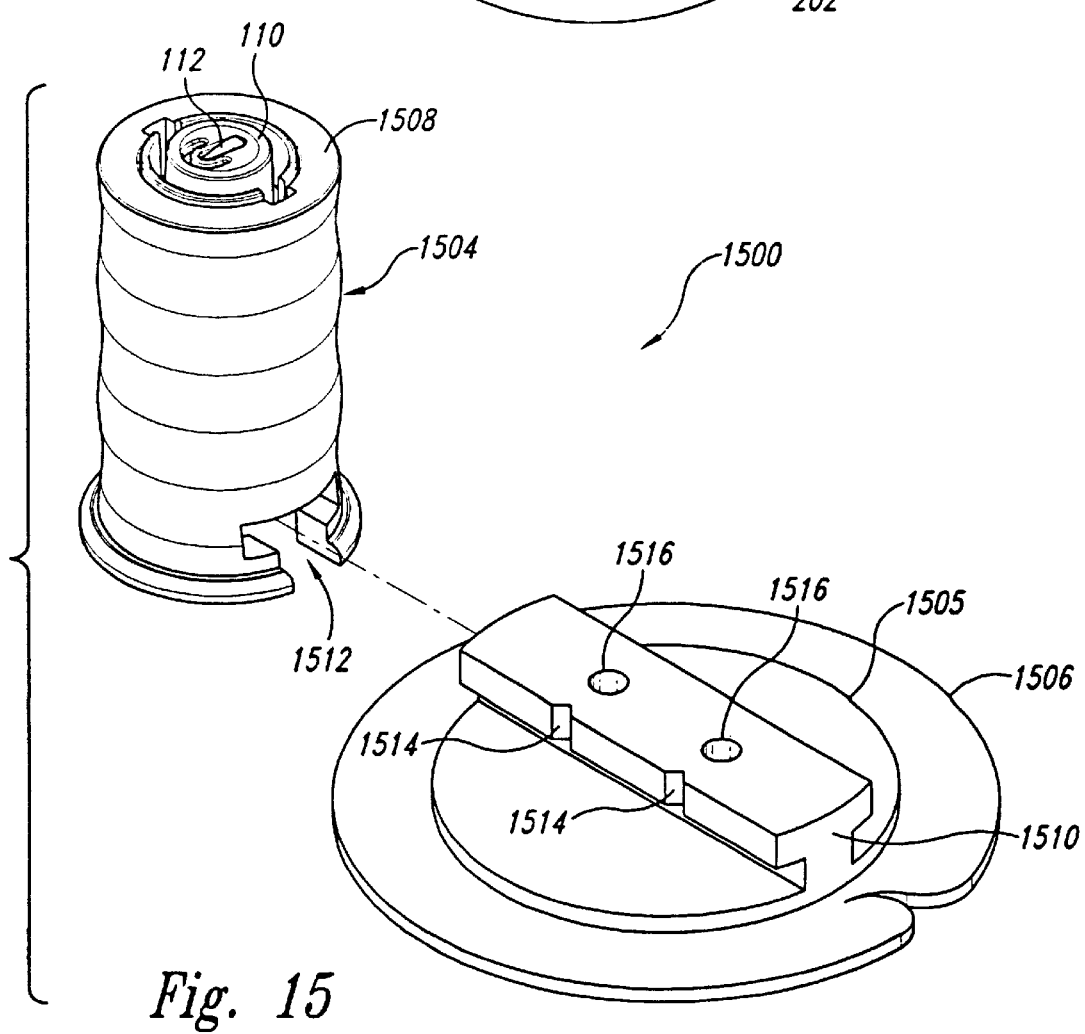
FIG. 15 is a partially exploded side isometric view of an applicator having a linearly actuated probe in accordance with another embodiment of the invention.

FIG. 15 is a partially exploded, side isometric view of a probe applicator 1500 having a linearly repositionable probe 112 in accordance with another embodiment of the invention. In one aspect of this embodiment, the probe 112 is housed in a slider 110 having a configuration generally similar to that described above. The slider 110 is positioned in a sleeve 1508 to move upwardly and downwardly relative to the sleeve 1508. The sleeve 1508 is fixedly positioned in a cylindrical base 1504. In a further aspect of this embodiment, the base 1504 includes a "T"-shaped slot 1512 extending through the base 1504 from one side to the other. The slot 1512 is configured to slidably receive a corresponding rail 1510 that projects upwardly from a base plate 1505. The base plate 1505 is mounted to an adhesive pad 1506 for attachment to the patient's skin 300 (FIG. 3) in a manner generally similar to that described above.

In a further aspect of this embodiment, the rail 1510 can include two probe apertures 1516 spaced laterally apart by a preselected distance. The base 1504 can be moved laterally along the rail 1500 to align the probe 112 with either the apertures 1516. In still another aspect of this embodiment, the rail 1510 can include notches 1514 aligned with the apertures 1516 and configured to receive a corresponding tab (not shown) of the base 1504 when the probe 112 is aligned with the corresponding aperture 1516. Accordingly, the practitioner can receive mechanical feedback indicating when the probe 112 is properly aligned with one of the apertures 1516.

In operation, the practitioner attaches the base plate 1505 to the skin 300 with the adhesive pad 1506 and aligns the slot 1512 of the base 1504 with the rail 1510 of the base plate 1505. The practitioner slides the base 1504 along the rail 1510 until the probe 112 is aligned with one of the probe apertures 1516, and inserts the probe 112 by moving the slider 110 downwardly with the actuator 200 (FIG. 2). If the probe 112 needs to be repositioned, the practitioner withdraws the probe 112 by moving the actuator 200 and the slider 110 upwardly, slides the base 1504 along the rail 1510 to the other probe aperture 1516 (with the probe moving linearly parallel to the skin 300), and reinserts the probe 112.

From the foregoing, it will be appreciated that specific embodiments of the invention have been described herein for purposes of illustration, but that various modifications may be made without deviating from the spirit and scope of the invention. Accordingly, the invention is not limited except as by the appended claims.

What is claimed is:

1. A method for operating a percutaneous probe, comprising:
    engaging a housing coupled to the probe with a selected location on a surface of a section of skin;
    inserting the probe into the skin at a first position on the surface of the skin; and
    withdrawing the probe from the first position and reinserting the probe into the skin at a second position on the surface of the skin by moving the probe relative to the housing while the housing remains in the selected location.

2. The method of claim 1, further comprising:
    moving the probe in a first direction relative to the housing and away from the skin without moving the probe in a second direction relative to the housing and aligned with the skin; and
    moving the probe in the second direction relative to the housing without moving the probe in the first direction relative to the housing.

3. The method of claim 1 wherein moving the probe relative to the housing includes orbiting the probe about an axis offset from a central axis of the housing.

4. The method of claim 1 wherein moving the probe relative to the housing includes moving the probe along a straight line in a plane aligned with and offset from the surface of the skin.

5. The method of claim 1 wherein the housing includes a plurality of channels and wherein the method further comprises halting movement of probe relative of the housing by inserting into one of the channels a tab coupled to the probe.

6. The method of claim 1, further comprising receiving mechanical feedback when the probe has moved from a first predetermined point relative to the housing to a second predetermined point relative to the housing.

7. The method of claim 1, further comprising:
overcoming a first level of mechanical resistance by moving the probe toward the skin to a first position with the probe spaced apart from the skin; and
moving the probe from the first position to a second position closer to the skin than the first position against a second level of mechanical resistance that is less than the first level of mechanical resistance.

8. The method of claim 1, further comprising overcoming mechanical resistance to move the probe from a first point where the probe is restricted from moving toward the skin to a second point where the probe can move freely toward the skin.

9. The method of claim 1, further comprising preventing movement of the probe from the first position to the second position while the probe is inserted in the skin.

10. The method of claim 1, further comprising releasably adhering the housing to the surface of the skin.

11. The method of claim 1 wherein the probe is an electrode and wherein inserting the probe includes inserting the electrode at a first position relative to a target nerve region beneath the skin, and wherein the method further comprises coupling the electrode to a source of electrical power to apply electrical stimulation to a region adjacent to the electrode.

12. The method of claim 1, further comprising simultaneously controlling an angle of entry of the probe into the skin while inserting the probe into the skin.

13. A method for operating a percutaneous electrode, comprising:
aligning with an external surface of a section of skin a housing that supports the percutaneous electrode;
engaging the housing with the surface of the skin;
inserting the electrode into the skin at a first position;
withdrawing the electrode from the skin by moving the electrode only in a direction generally normal to the surface of the skin while maintaining the housing in an approximately constant location relative to the skin;
rotating the electrode relative to the housing from the first position to a second position spaced apart from the first position without engaging the electrode with the surface of the skin; and
reinserting the electrode into the skin at the second position.

14. The method of claim 13 wherein the electrode is coupled to a guide member that is received in a housing channel extending away from the skin, and further wherein withdrawing the electrode includes moving the guide member away from the skin in the channel.

15. The method of claim 13 wherein the electrode is coupled to a locator tab, and wherein rotating the electrode relative to the housing includes rotating the locator tab from a first channel of the housing to a second channel of the housing spaced apart from the first channel.

16. The method of claim 13 wherein the housing includes an axial restriction having a first side facing away from the skin and a second side facing toward the skin and the electrode is coupled to a guide member having a portion adjacent to the first side of the axial restriction, and wherein reinserting the electrode includes moving the guide member from the first side of the axial restriction to the second side of the axial restriction.

17. The method of claim 13, further comprising coupling the electrode to a source of electrical power to apply electrical stimulation to a region adjacent to the electrode.

18. The method of claim 13, further comprising at least inhibiting rotation of the electrode relative to the housing while the electrode is inserted into the skin.

19. A method for treating a patient with percutaneous electrical stimulation, comprising:
releasably attaching a percutaneous electrode housing to an external surface of a section of skin;
positioning a guide member of a slider that supports the electrode at least partially within a first axial channel of a sleeve within the housing;
inserting the electrode into the skin at a first selected position relative to a target nerve region beneath the skin by engaging the slider with a plunger and moving the slider and the plunger together toward the skin with the guide member of the slider in the first axial channel of the sleeve and a peg of the plunger in a first axial channel of the housing, the first axial channel of the housing being coextensive with the first axial channel of the sleeve;
withdrawing the electrode from the skin in a direction generally normal to the external surface of the skin by sliding the slider away from the skin while maintaining the housing at an approximately constant position relative to the skin and while at least restricting transverse movement of the electrode relative to the surface of the skin;
orbiting the electrode about a central axis of the housing from the first selected position to a second selected position spaced apart from the first selected position without moving the electrode toward or away from the skin by rotating the sleeve, the slider, the electrode and the plunger together as a unit relative to the housing until the peg of the plunger is positioned within a second axial channel of the housing;
reinserting the electrode into the skin at the second selected position by sliding the slider member toward the skin; and
applying electrical power to the electrode.

20. The method of claim 19 wherein the sleeve has a sleeve tab and rotating the sleeve includes disengaging the sleeve tab from one axial channel in the housing and reinserting the sleeve tab in another axial channel of the housing.

21. A method for manufacturing a device for penetrating skin, comprising:
positioning a probe in a slider member;
disposing the slider member in a cavity of a housing with the probe being generally parallel to and offset from a major axis of the cavity and the slider member being slideable relative to the housing along an axis aligned with the probe; and
at least restricting motion of the slider member out of the cavity by at least restricting rotational motion of the slider member in one direction relative to the housing.

22. The method of claim 21 wherein the housing includes a first portion defining a first portion of the cavity and is pivotably coupled to a second portion defining a second portion of the cavity, and wherein the method further comprises positioning the slider member between the first and second portions of the housing and pivoting at least one of the first and second portions of the housing toward the other to receive a first part of the slider member in the first portion of the cavity and receive a second part of the slider member in the second portion of the cavity.

23. The method of claim 21 wherein the housing includes two internal ramped stop members, each stop member having an inclined surface with a first end and a second end, each stop member further having a stop surface extending away from the second end of the inclined surface, and wherein the method further comprises:

engaging first and second guide tabs of the slider member with the first ends of the inclined surfaces of the ramps;

rotating the slider member relative to the housing to move the first and second guide tabs along the inclined surfaces of the ramps; and further rotating the slider member relative to the housing to move each tab beyond the second end of one of the inclined surfaces with each tab facing one of the stop surfaces.

24. A method for manufacturing a device for penetrating skin, comprising:

positioning a probe in a slider member;

positioning slider member between first and second pivotably coupled portions of a housing body, the first portion of the housing body having a first cavity and the second portion of the housing body having a second cavity; and pivoting at least one of the first and second portions of the housing body toward the other to receive a first part of the slider member in the first cavity and receive a second part of the slider member in the second cavity.

25. The method of claim 24, further comprising fixedly positioning the probe along an axis generally parallel to and offset from a major axis of the housing body.

26. The method of claim 24, further comprising at least restricting motion of the slider out of the cavity by at least restricting rotational motion of the slider in one direction relative to the housing body.

27. An apparatus for piercing a skin surface, comprising:

a support housing having a casing defining an axial direction and an engaging surface to engage the skin surface at one end of the casing; and a probe moveably supported relative to the support housing and moveable relative to the support housing in an axial direction toward and away from the engaging surface between a first position a first distance from the engaging surface and a second position a second distance from the engaging surface greater than the first distance, and the probe being moveable transverse to the axial direction relative to the support housing only when the probe is in the second position.

28. The apparatus of claim 27 wherein the probe is supported by a slider member having at least one guide portion, further wherein the support housing has at least one axial channel coupled to at least one transverse channel, the guide portion being received in the axial channel to move toward and away from the engaging surface, the guide portion being sequentially received in the transverse channel to move transverse to the engaging surface.

29. The apparatus of claim 27 wherein the probe includes an electrode coupleable to a source of electrical power.

30. The apparatus of claim 27 wherein the support housing includes:

a base having the engagement surface and a receiving cylinder projecting away from the engagement surface along a central axis, the receiving cylinder having an inner surface and a plurality of axial channels in the inner surface; and a sleeve positioned within the receiving cylinder, the sleeve having at least one tab projecting into a corresponding one of the axial channels in the cylinder, the sleeve further having an internal cavity elongated along the central axis, the sleeve being rotatable relative to the base about the central axis and having a plurality of sleeve channels coextensive with the axial channels of the base.

31. An apparatus for piercing a skin surface, comprising:

a support housing having an engaging surface to engage a surface of a section of skin, the support housing having a first guide extending axially away from the engaging surface and a second guide extending transverse to the first guide; and a probe coupled to a guide member, the guide member sequentially engaged with the first guide and the second guide to move in a first direction toward and away from the engaging surface without simultaneously moving in a second direction transverse to the first direction, and move in the second direction without simultaneously moving in the first direction.

32. The apparatus of claim 31 wherein the probe includes an electrode coupleable to a source of electrical power.

33. The apparatus of claim 31 wherein the first guide includes a first channel, the second guide includes a second channel, and the guide member is slideably received sequentially in the first and second channels.

34. The apparatus of claim 31 wherein the support housing includes:

a base having the engagement surface and a receiving cylinder projecting away from the engagement surface along a central axis, the receiving cylinder having an inner surface and a plurality of axial channels in the inner surface; and a sleeve positioned within the receiving cylinder, the sleeve having at least one tab projecting into a corresponding one of the axial channels in the cylinder, the sleeve further having an internal cavity elongated along the central axis, the sleeve being rotatable relative to the base about the central axis and having a plurality of sleeve channels coaxial with the axial channels of the base.

35. A replaceable cartridge for use with a plunger having an electrical contact for administering percutaneous electrical stimulation, comprising:

a support housing having a generally flat engagement surface to engage a section of skin, the support housing further having a receiving cylinder projecting away from the engagement surface along a first axis;

a slider member positioned within the receiving cylinder and having at least one plunger engaging surface to removably engage the plunger; and an electrode projecting away from the slider member along a second axis offset from and at least approximately parallel to the first axis, the electrode being coupleable to the electrical contact of the plunger.

36. The apparatus of claim 35 wherein the support housing includes:

a base having the engagement surface and a receiving cylinder projecting away from the engagement surface along a central axis, the receiving cylinder having an inner surface and a plurality of axial channels in the inner surface; and a sleeve positioned within the receiving cylinder, the sleeve having at least one tab projecting into a corresponding one of the axial channels in the cylinder, the sleeve further having an internal cavity elongated along the central axis, the sleeve being rotatable relative to the base about the central axis and having a plurality of sleeve channels coaxial with the axial channels of the base.

37. An apparatus for providing percutaneous electrical stimulation, comprising:

a base having a generally flat engagement surface to engage the skin of a recipient, the base further having a receiving cylinder projecting away from the engagement surface along a first axis, the receiving cylinder having an inner surface and a plurality of axial channels in the inner surface;

a sleeve positioned within the receiving cylinder, the sleeve having at least one tab projecting into a corresponding one of the axial channels in the cylinder, the sleeve further having an internal cavity elongated along the first axis, the sleeve being rotatable relative to the base about the first axis, the sleeve further having two transverse channel portions, each transverse channel portion being proximate to a first axial stop member and a first rotational stop member, each transverse channel portion being coupled to an axial channel portion aligned with one of the axial channels of the base;

a slider positioned within the internal cavity of the sleeve, the slider having an electrode aperture aligned with a second axis that is parallel to and offset from the first axis, the slider further having two slots extending circumferentially about the first axis, the slider still further having a second axial stop member to engage the first axial stop member of the sleeve and a second rotational stop member to engage the first rotational stop member of the sleeve;

an electrode positioned within the electrode aperture of the slider and projecting away from the slider along the second axis, the electrode being coupleable to a source of electrical power; and a plunger elongated along the first axis and having two plunger pegs, each plunger peg extending radially outwardly through one of the slots of the slider to engage the slider and drive the slider axially relative to the sleeve between a retracted position with the electrode positioned within the receiving cylinder and an extended position with the electrode projecting from the receiving cylinder beyond the base, each plunger peg further extending radially outwardly into one of the axial channels of the sleeve, with the plunger, the slider and the sleeve being rotatable as a unit about the first axis to orbit the electrode about the first axis, each plunger peg still further extending radially outwardly into one of the axial channels of the base.

38. The apparatus of claim 37 wherein the sleeve has a retaining groove transverse to the first axis and the sleeve has a lip received in the retaining groove to at least restrict axial motion of the sleeve relative to the base.

39. An apparatus for delivering percutaneous electrical stimulation, comprising:

a support housing having an engaging surface to engage a surface of a section of skin, the support housing having a first guide extending axially away from the engaging surface and a second guide extending transverse to the first guide;

an electrode having a sharp end and coupled to a guide member, the guide member having an engaging portion sequentially engaged with the first guide and the second guide to move in a first direction toward and away from the engaging surface without simultaneously moving in a second direction transverse to the first direction, and move in the second direction without simultaneously moving in the first direction;

an electrical contact releasably coupled to the electrode;

an electrical power source; and an electrical link coupled between the electrical power source and the electrical contact.

40. The apparatus of claim 39 wherein the first guide includes an axial channel, the second guide includes a transverse channel and the guide member is sequentially received in the first and second channels.

* * * * *

UNITED STATES PATENT AND TRADEMARK OFFICE
CERTIFICATE OF CORRECTION

PATENT NO. : 6,529,776 B1
DATED : March 4, 2003
INVENTOR(S) : Leonard et al.

It is certified that error appears in the above-identified patent and that said Letters Patent is hereby corrected as shown below:

<u>Title page,</u>
Item [56], References Cited, U.S. PATENT DOCUMENTS, insert: --

| | | |
|---|---|---|
| 3,030,959 | 4/24/62 | Grunert |
| 3,090,151 | 5/21/63 | Stewart et al. |
| 3,208,452 | 9/28/65 | Stern |
| 3,938,526 | 2/17/76 | Anderson et al. |
| 3,943,935 | 3/16/76 | Cameron |
| 3,983,881 | 10/5/76 | Wickham |
| 4,139,011 | 2/13/79 | Benoit et al. |
| 4,207,903 | 6/17/80 | O'Neill |
| 4,256,116 | 3/17/81 | Meretsky et al. |
| 4,262,672 | 4/21/81 | Keif |
| 4,281,659 | 8/4/81 | Farrar et al. |
| 4,408,617 | 10/11/83 | Auguste |
| 4,431,000 | 2/14/84 | Butler et al. |
| 4,512,351 | 4/23/85 | Pohndorf |
| 4,541,432 | 9/17/85 | Molina-Negro et al. |
| 4,556,064 | 12/3/85 | Pomeranz et al. |
| 4,685,466 | 8/11/87 | Rau |
| 4,712,558 | 12/15/87 | Kidd et al. |
| 4,765,310 | 8/23/88 | Deagle et al. |
| 4,895,154 | 1/23/90 | Bartelt et al. |
| 4,934,371 | 6/19/90 | Malis et al. |
| 4,953,564 | 9/4/90 | Berthelsen |
| 5,012,811 | 5/7/91 | Malis et al. |
| 5,036,850 | 8/6/91 | Owens |
| 5,054,486 | 10/8/91 | Yamada |
| 5,094,242 | 3/10/92 | Gleason et al. |
| 5,117,826 | 6/2/92 | Bartelt et al. |
| 5,211,175 | 5/18/93 | Gleason et al. |
| 5,246,014 | 9/21/93 | Williams et al. |
| 5,255,291 | 10/26/93 | Otten |
| 5,281,218 | 1/25/94 | Imran |
| 5,332,401 | 7/26/94 | Davey et al. |
| 5,423,314 | 6/13/95 | Schmid |
| 5,439,440 | 8/8/95 | Hofmann |
| 5,449,378 | 9/12/95 | Schouenborg |
| 5,810,762 | 9/22/98 | Hofmann |
| 5,861,015 | 1/19/99 | Benja-Athon |
| 5,873,849 | 2/23/99 | Bernard |
| 5,928,144 | 7/27/99 | Real |
| 5,941,845 | 8/24/99 | Tu et al. |
| 5,948,008 | 9/7/99 | Daikusono |
| 5,968,063 | 10/19/99 | Chu et al. |
| 6,009,347 | 12/28/99 | Hofmann |
| 6,035,236 | 3/7/00 | Jarding et al. |
| 6,050,992 | 4/18/00 | Nichols |
| 6,068,650 | 5/30/00 | Hofmann et al. |
| 6,122,547 | 9/19/00 | Benja-Athon |
| 6,208,893 | 3/27/01 | Hofmann |
| Des 297,047 | 8/2/88 | Hon et al. |
| Des 318,330 | 7/16/91 | Doty et al. |
| Des 357,069 | 4/4/95 | Plahn et al. |
| 09,667,183 | 9/21/00 | Leonard |

UNITED STATES PATENT AND TRADEMARK OFFICE
CERTIFICATE OF CORRECTION

PATENT NO. : 6,529,776 B1
DATED : March 4, 2003
INVENTOR(S) : Leonard et al.

It is certified that error appears in the above-identified patent and that said Letters Patent is hereby corrected as shown below:

Item [56], References Cited, OTHER PUBLICATIONS, insert:

AAMI Neurosurgery Committee; AAMI Implantable Neurostimulator Subcommittee. Implantable peripheral nerve stimulators. Assoc. for the Advancement of Medical Instrumentation (1995) NS15-1995, cover-8, 11 pages.

AHMED et al., "Percutaneous Electrical Nerve Stimulation (PENS): A Complimentary Therapy for the Management of Pain Secondary to Bony Metastasis", Clinical Journal of Pain (December 1998) 14:320-3

AHMED et al., "Percutaneous Electrical Nerve Stimulation: An Alternative to Antiviral Drugs for Herpes Zoster," Anesth. Analg. (October 1998) 87:911-4

ALMAY, B.G.L. et al., "Long-Term High Frequency Transcutaneous Electrical Nerve Stimulation (hi-TNS) in Chronic Pain. Clinical Response and Effects of CSF-Endorphins, Monoamine Metabolites, Substance P-Like Immunoreactivity (SPLI) and Pain Measures", J. Physchosom.Res. (1985) 29:247-257, 11 pages.

BAKER, L. et al., "Effects of Waveform on Comfort During Neuromuscular Electrical Stimulation", Clinical Orthopedics and Related Research (August 1988) 233:75-85

BALLEGAARD et al., "Acupuncture and Transcutaneous Electric Nerve Stimulation in the Treatment of Pain Associated with Chronic Pancreatitis", Scan.J.Rehab.Med. (December 1985) 20:1249-54

BALOGUN et al., "The effects of acupuncture, electroneedling and transcutaneous electric nerve stimulation therapies on peripheral haemodynamic functioning", Disability and Rehab. (February 1998) 20:41-8

BALOGUN, J., "Effects of Ramp Time on Sensory, Motor and Tolerance Thresholds During Exogenous Electrical Stimulation", The Journal of Sports Medicine and Physical Fitness (December 1991) 3:4, 521-526

BD Safety Products. BD Vacutainer Safety-Lok Blood Collection Set; BD Vacutainer SafetyGlide Blood Collection Assembly and BD Vacutainer Eclipse Blood Collection Needle, 1 page.

BD Safety Flow Lancet – Product Number 366356. BD catalog 1997-2000, Capillary Access, http://catalog.bd.com/scripts/OBDsheet.exe?FNC=productlist_Alistproducts_html_366356 (08/07/2001) (3 pages).

BD Vacutainer SafetyGlide Blood Collection Assembly. Quick Reference Card (1999), 1 page.

BRULL, S., SILVERMAN, D.G., "Pulse Width, Stimulus Intensity, Electrode Placement, and Polarity During Assessment of Neuromuscular Block", Anesthesiology (10/1995) 83:702-709

BUSHNELL et al., "Electrical stimulation of peripheral and central pathways for the relief of musculoskeletal pain", Can.J.Physiol.Pharmacol. (May 1991) 69:697-703

CARROLL, D., "Randomization is Important in Studies with Pain Outcomes: Systematic Review of Transcutaneous Electrical Nerve Stimulation in Acute Postoperative Pain", Br J Anaesth. (1996) 77:798-803

CASSUTO, J. et al., "The Use of Modulated Energy Carried on a High Frequency Wave for the Relief of Intractable Pain", Int.J.Clin.Pharm.Res. (1993) XIII(4) 239-241

UNITED STATES PATENT AND TRADEMARK OFFICE
CERTIFICATE OF CORRECTION

PATENT NO. : 6,529,776 B1
DATED : March 4, 2003
INVENTOR(S) : Leonard et al.

Page 3 of 7

It is certified that error appears in the above-identified patent and that said Letters Patent is hereby corrected as shown below:

CHENG et al., "Electroacupuncture analgesia could be mediated by at least two pain-relieving mechanisms: endorphin and non-endorphin systems", Life Sciences (December 3, 1979) 25:1957-62

CHENG et al., "Electroacupuncture elevates blood cortisol levels in naïve horses; sham treatment has no effect", Intern.J.Neuroscience (1980) 10:95-7 (1980/no month listed)

CHENG et al., "Electrotherapy of Chronic Musculoskeletal Pain: Comparison of Electroacupuncture and Acupuncture-Like Transcutaneous Electrical Nerve Stimulation", Clin.J.Pain (1987) 2:143-9 (1987)

CRAMP AF et al., "The Effect of High and Low Frequency Transcutaneous Electrical Nerve Stimulation Upon Cutaneous Blood Flow and Skin Temperature in Healthy Subjects", Clin.Physio. (2000) 20:150-7

Eclipse+ Dual Channel Transcutaneous Electrical Nerve Stimulator User's Manual (1993), 31 pages Electrotherapy for Rehabilitation, Empi Cervical Traction, http://www.empi.com/b/b2.htm, 10/22/01, 3 pages.

Electrotherapy for Rehabilitation, Empi Cervical Traction, http://www.empi.com/b/b2.htm, 3/23/01, 8 pages.

EPIX XL TENS Instruction Manual, Empi, Inc. (1988), 21 pages

FOSTER, N. et al., Manipulation of Transcutaneous Electrical Nerve Stimulation Variables Has No Effect on Two Models of Experimental Pain in Humans", The Clinical Journal of Pain (1996) 12:301-310

GADSBY et al., "Nerve stimulation for low back pain - a review," Nursing Standard 11:32-3 (July 16, 1997)

GALLETTI S.P. et al., Highlights concerning low frequency-high intensity TENS (review). Minerva Stomatol (1995) 44:421-9

GHONAME et al., "Does the Stimulus Frequency Affect the Analgesic Response to Electrical Stimulation?", Anesth. Analg. (1999) 88:S210, 1 page.

GHONAME et al., "Percutaneous Electrical Nerve Stimulation for Low Back Pain", JAMA (March 3, 1999) 281:818-23

GHONAME et al., "Percutaneous electrical nerve stimulation: an alternative to TENS in the management of sciatica", Pain (November 1999) 83:193-9

GHONAME et al., "The Effect of Stimulus Frequency on the Analgesic Response to Percutaneous Electrical Nerve Stimulation in Patients with Chronic Low Back Pain", Anesth.Analg. (April 1999) 88:841-6

GHONAME et al., "The Effect of the Duration of Electrical Stimulation on the Analgesic Response", Anesth.Analg. (1999) 88:S211

GOPALKRISHNANN, P., SLUKA, K.A., "Effect of Varying Frequency, Intensity, and Pulse Duration of Transcutaneous Electrical Nerve Stimulation on Primary Hyperalgesia in Inflamed Rats", Arch.,Phys.Med.Rehabil. (7/2000) 81:984-990

GRACANIN, F., TRNKOCZY, A. "Optimal Stimulus Parameters for Minimum Pain in the Chronic Stimulation of Innervated Muscle", Arch.Phys.Med. Rehabil. (June 1975) 56:243-249

HAMZA, M.A. et al., "Effect of the Duration of Electrical Stimulation on the Analgesic Response in Patients with Low Back Pain", Anesthesiology (December 1999), V. 91, No. 6:1622-7.

HAMZA MA et al., "Effect of the frequency of transcutaneous electrical nerve stimulation on the postoperative opioid analgesic requirement and recovery profile", Anesthesiology (November 1999) 91:1232-8

HAN JS et al., "Effect of Low and High-Frequency TENS on Met-enkephalin-Arg-Phe and Dynorphin A Immunoreacitivity in Human Lumbar CSF", Pain (1991) 47:295-8

Healthronics HANS LY257 User Manual, 15 pages.

Innovative Healthcare: Electrotherapy Pain & Rehabilitation Product Solutions from Rehabilicare. [Includes product description of SporTX and Ortho DX]. 1999, 3 pages, http://www.mvpdesign.com/sites/rehavilicare/all_products.html Instruction Manual for the Empi EPIX VT TENS Device, 1997, Dual Channel Transcutaneous Electrical Nerve Stimulator, Empi, Inc., 29 pages.

UNITED STATES PATENT AND TRADEMARK OFFICE
CERTIFICATE OF CORRECTION

PATENT NO. : 6,529,776 B1
DATED : March 4, 2003
INVENTOR(S) : Leonard et al.

It is certified that error appears in the above-identified patent and that said Letters Patent is hereby corrected as shown below:

Intelect Legend Stim Clinical Reference Manual, Volume 4 Intelect Legend Series, Chattanooga Group, Inc.. 31 pages.

JETTE, D., "Effect of Different Forms of Transcutaneous Electrical Nerve Stimulation on Experimental Pain", Physical Therapy (February 1986) 66:2, 187-193

JOHNSON, M.I., "Analgesic Effects of Different Pulse Patterns of Trancutaneous Electrical Nerve Stimulation on Cold-induced Pain in Normal Subjects", Journal of Psychosomatic Research (1991) 35:2-3; 313-321

JOHNSON, MI, "Analgesic Effects of Different Frequencies of Transcutaneous Electrical Nerve Stimulation on Cold-Induced Pain in Normal Subjects", Pain (1989) 39:231-6

JOHNSON, MI, et al. "An In-Depth Study of Long Term Users of Transcutaneous Electrical Nerve Stimulation (TENS). Implications for Clinical Use of TENS", Pain (1991) 44:221-9

KATIMS, J.J. et al., "Transcutaneous Nerve Stimulation. Frequency and Waveform Specificity in Humans", Appl. Neurophysiol (1986) 49:86-91

LANDAU et al., "Neuromodulation Techniques for Medically Refractory Chronic Pain", Annu.Rev.Med. 44:279-87 (1993)/no month listed (annual publication)

LEEM, J., "Electrophysiological evidence for the antinociceptive effect of transcutaneous electrical stimulation on mechanically evoked responsiveness of dorsal horn neurons in neuropathic rats", Neuroscience Letters (1995) 192:197-200

LEHMANN et al., "Efficacy of Electroacupuncture and TENS in the Rehabilitation of Chronic Low Back Pain Patients", Pain (September 1986) 26:277-90

LISS S., LISS B., "Physiological and Therapeutic Effects of High Frequency Electrical Pulses", Integr.Physio.Behav. Sci. (April-June 1996) 31:88-94

Model AWQ-104B Multi-Purpose Electronic Acupunctoscope Instruction Manual, 10 pages MARCHAND, S., et al., "Modulation of Heat Pain Perception by High Frequency Transcutaneous Electrical. Nerve Stimulation (TENS)", Clin.J.Pain (1991) 7:122-9

MORENO-ARANDA J., "Electrical Parameters for over-the-skin muscle stimulation", J. Biomechanics (1981) 14:9, 579-585

MORENO-ARANDA J., SEIREG, A., "Investigation of over-the-skin electrical stimulation parameters for different normal muscles and subjects", J. Biomechanics (1981) 14:9; 587-593

O'BRIEN, WJ, "Effect of Transcutaneous Electrical Nerve Stimulation on Human Blood B-Endorphin Levels", Physical Therapy (September 1984) 64:1367-1374

OMURA, Y., "Basic electrical parameters for safe and effective electro-therapeutics [electroacupuncture, TES, TENMS (or TEMS), TENS and electro-magnetic field stimulation with or without drug field] for pain, neuromuscular skeletal problems, and circulatory disturbances", Acupuncture & Electro-Therapeutics Res. (1987) 12:201-25

OMURA, Y., "Electrical parameters for safe and effective electro-acupuncture and transcutaneous electrical stimulation: Threshold potentials for tingling, muscle contraction and pain; and how to prevent adverse effects of electro-therapy", Acupuncture & Electro-Therapeutics Res. 10:335-7 (1985)

ORDOG, G., "Transcutaneous Electrical Nerve Stimulation Versus Oral Analgesic: A Randomized Double-Blind Controlled Study in Acute Traumatic Pain", American Journal of Emergency Medicine (January 1987) 5:1, 6-10

Ortho DX Product Data Sheet

Pointer F-3 Instruction Manual, ITO Co., Ltd., 10 pages.

RADIONICS RFG-3C product brochure (1997), 10 pages.

Rehabilicare Ortho Dx product brochure, 2 pages.

REHABILICARE SporTX product brochure, 2 pages.

UNITED STATES PATENT AND TRADEMARK OFFICE
CERTIFICATE OF CORRECTION

PATENT NO. : 6,529,776 B1
DATED : March 4, 2003
INVENTOR(S) : Leonard et al.

It is certified that error appears in the above-identified patent and that said Letters Patent is hereby corrected as shown below:

ROMITA et al., "Parametric Studies on Electroacupuncture-Like Stimulation in a Rat Model: Effects of Intensity, Frequency, and Duration of Stimulation on Evoked Antinociception", Brain Res.Bull. (1997) 42\289 96

ROONEY, J.G., et al., "Effect of Variation in the Burst and Carrier Frequency Modes of Neuromuscular Electrical Stimulation on Pain Perception of Healthy Subjects", Phys.Ther. (November 1992) 72:11, 800-808

SLUKA, K.A., "Treatment with Either High or Low Frequency TENS Reduces the Secondary Hyperalgesia Observed After Injection of Kaolin and Carrageenan into the Knee Joint", Pain (1998) 77:97-102

SMP-plus. The Pain Relief Solution for Hard to Treat Patients, Rehabilicare (2 pages).

SOMERS, D.L., "High-Frequency Transcutaneous Electrical Nerve Stimulation Alters Thermal but not Mechanical Allodynia Following Chronic Constriction Injury of the Rat Sciatic Nerve", Arch.Phys.Med.Rehabil. (November 1998) 79:1370-6

SPORTX Product Data Sheet

STAROBINETS, M., VOLKOVA, L., [Analgesic Effect of High-Frequency and Acupuncture-Like Trancutaneous Electric Stimulation of Nerve Fibers in Spinal Osteochondritis]. Zh Nevropatol Psikhiatr Im S. S. Korsakova (1985) 85-350-4

ULETT et al., "Electroacupuncture: Mechanicsms and Clinical Application," Biol. Psych. 44:129-38 (July 15, 1998)

VAN DOREN, CL, "Contours of Equal Perceived Amplitude and Equal Perceived Frequency for Electrocutaneous Stimuli", Percept.Phychophys. (1997) 59:613-22

WHITE, P.F. et al., "Percutaneous Neuromodulation Therapy: Does the Location of Electrical Stimulation Effect the Acute Analgesic Response?", Anesth. Analg. (2000) 91:1-6

WHITE, P.F. et al., "The Effect of Montage on the Analgesic Response to Percutaneous Neuromodulation Therapy", Anesth. Analg. (2001) 92:483-7

U.S. Patent Application No. 09/452,477, entitled "PERCUTANEOUS ELECTRICAL THERAPY SYSTEM WITH ELECTRODE ENTRY ANGLE CONTROL," filed on December 1, 1999, Attorney Docket No. 337348004US.

U.S. Patent Application No. 09/452,663, entitled "PERCUTANEOUS ELECTRICAL THERAPY SYSTEM PROVIDING ELECTRODE AXIAL SUPPORT," filed on December 1, 1999, Attorney Docket No. 337348005US.

U.S. Patent Application No. 09/452,508, entitled "PERCUTANEOUS ELECTRICAL THERAPY SYSTEM WITH ELECTRODE DEPTH CONTROL," filed on December 1, 1999, Attorney Docket No. 337348006US.

U.S. Patent Application No. 09/451,795 entitled "PERCUTANEOUS ELECTRICAL THERAPY SYSTEM WITH POSITION MAINTENANCE," filed on December 1, 1999, Attorney Docket No. 337348007US.

U.S. Patent Application No. 09/451,799 entitled "ELECTRODE INTRODUCER FOR A PERCUTANEOUS ELECTRICAL THERAPY SYSTEM," filed on December 1, 1999, Attorney Docket No. 337348008US.

U.S. Patent Application No. 09/452,510, entitled "PERCUTANEOUS ELECTRICAL THERAPY SYSTEM FOR MINIMIZING ELECTRODE INSERTION DISCOMFORT," filed on December 1, 1999, Attorney Docket No. 337348009US.

U.S. Patent Application No. 09/451,800, entitled "ELECTRODE ASSEMBLY FOR A PERCUTANEOUS ELECTRICAL THERAPY SYSTEM," filed on December 1, 1999, Attorney Docket No. 337348010US.

U.S. Patent Application No. 09/451,796, entitled "ELECTRODE REMOVER FOR A PERCUTANEOUS ELECTRICAL THERAPY SYSTEM," filed on December 1, 1999, Attorney Docket No. 337348011US.

U.S. Patent Application No. 09/451,547, entitled "PERCUTANEOUS ELECTRICAL THERAPY SYSTEM WITH SHARP POINT PROTECTION," filed on December 1, 1999, Attorney Docket No. 337348012US -- after "Neilsen et al." --;

UNITED STATES PATENT AND TRADEMARK OFFICE
CERTIFICATE OF CORRECTION

PATENT NO.    : 6,529,776 B1
DATED         : March 4, 2003
INVENTOR(S)   : Leonard et al.

It is certified that error appears in the above-identified patent and that said Letters Patent is hereby corrected as shown below:

Column 2,
Line 49, "front" should be -- from --;
Line 60, delete comma between "an" and "electrical";

Column 3,
Lines 44 and 45, "identity" should be -- identify --;

Column 5,
Line 7, "300," should be -- 300. --;
Lines 37 and 67, insert comma between "embodiment" and "the";
Line 67, "ran" should be -- can --;

Column 7,
Line 8, "below," should be -- below. --;
Line 23, "306," should be -- 306. --;
Line 48, delete comma between "assembly" and "pegs";

Column 8,
Line 1, "tile" should be -- the --;
Line 50, "200)" should be -- 200 --;
Line 51, "509" should be -- 508 --;

Column 9,
Line 2, "file" should be -- the --;
Line 64, "10" should be -- 110 --;

UNITED STATES PATENT AND TRADEMARK OFFICE
CERTIFICATE OF CORRECTION

PATENT NO.   : 6,529,776 B1
DATED        : March 4, 2003
INVENTOR(S)  : Leonard et al.

It is certified that error appears in the above-identified patent and that said Letters Patent is hereby corrected as shown below:

Column 10,
Line 23, "corrected" should be -- connected -;

Column 15,
Line 28, insert -- the -- between "positioning" and "slider";

Signed and Sealed this

Nineteenth Day of August, 2003

JAMES E. ROGAN
*Director of the United States Patent and Trademark Office*